US009321817B2

(12) United States Patent
Ficht et al.

(10) Patent No.: US 9,321,817 B2
(45) Date of Patent: Apr. 26, 2016

(54) HSP20 INHIBITS AMYLOIDOGENESIS AND NEUROTOXICITY

(71) Applicant: The Texas A&M University System, College Station, TX (US)

(72) Inventors: Allison Ficht, College Station, TX (US); Theresa Good, Pasadena, MD (US); Kenneth Carson, San Antonio, TX (US); Sungmun Lee, Seoul (KR)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 14/251,709

(22) Filed: Apr. 14, 2014

(65) Prior Publication Data
US 2014/0303088 A1      Oct. 9, 2014

Related U.S. Application Data

(62) Division of application No. 11/139,770, filed on May 26, 2005, now Pat. No. 8,710,009.

(60) Provisional application No. 60/575,758, filed on May 26, 2004.

(51) Int. Cl.
| A61K 38/17 | (2006.01) |
| A61K 39/00 | (2006.01) |
| A61K 39/002 | (2006.01) |
| C07K 14/44 | (2006.01) |
| A61K 38/00 | (2006.01) |

(52) U.S. Cl.
CPC ........ *C07K 14/44* (2013.01); *A61K 38/00* (2013.01)

(58) Field of Classification Search
None
See application file for complete search history.

(56) References Cited

U.S. PATENT DOCUMENTS

| 438,183 A | 10/1890 | Rishel |
| 5,817,626 A | 10/1998 | Findeis et al. |
| 6,787,143 B1 | 9/2004 | Schenk |
| 8,710,009 B2 | 4/2014 | Ficht et al. |

OTHER PUBLICATIONS

Norimine et al., Conservation of Babesia bovis Small Heat Shock Protein (Hsp20) among Strains and Definition of T Helper Cell Epitopes Recognized by Cattle with Diverse Major Histocompatibility Complex Class II Haplotypes. Infection and Immunity, Feb. 2004, p. 1096-1106.*
Abgar, et al., "Study of the Chaperoning Mechanism of Bovine α-Crystallin, a Member of the α-Small Heat Shock Superfamily," Biophys J (2001), 80:1986-95.
Brown, et al., "A novel 20-kilodalton protein conserved in Babesia bovis and B. bigemina stimulates memory CD4(+) T lymphocyte responses in B. bovis-immune cattle," Mol Biochem Parasitol (2001), 118:97-109.
Bruey, et al., "Hsp27 negatively regulates cell death by interacting with cytochrome c," Nat Cell Biol (2000), 2:645-52.
Cairo, et al., "Affinity-Based Inhibition of β-Amyloid Toxicity," (2002) Biochemistry (2002), 41:8620-9.

(Continued)

*Primary Examiner* — Gregory S Emch
*Assistant Examiner* — Aurora M Fontainhas
(74) *Attorney, Agent, or Firm* — Edwin S. Flores; Daniel J. Chalker; Chalker Flores, LLP

(57) ABSTRACT

The present inventions are compositions and methods of using at least a portion of an isolated and purified α-crystallin polypeptide that includes one or more β-pleated sheets and that prevents neurotoxicity and amyloidogenesis.

15 Claims, 15 Drawing Sheets

(56) References Cited

OTHER PUBLICATIONS

Clark, et al., "Small Heat-Shock Proteins and Their Potential Role in Human Disease," Curr. Opin. Struct. Biol. (2000), 10:52-59.
Dahlgren, et al., "Oligomeric and Fibrillar Species of Amyloid-β2 Peptides Differentially Affect Neuronal Viability," J Biol Chem (2002), 277:32046-53.
Hatters, et al., "The Molecular Chaparone, 60 -Crystallin, Inhibits Amyloid Formation by Apolipoprotein C-II," J Biol Chem (2001), 276:33755-61.
Hetenyi, et al., "Pentapeptide Amides Interfere with the Aggregation of 62 -Amyloid Peptide of Alzheimer's Disease," (2002) Biochem Biophys Res Commun (2002), 292:931-6.
Horwitz, J. "The function of alpha-crystallin in vision," (2000) Semin Cell Dev Biol (2000), 11:53-60.
Hughes, et al., "60 2-Macroglobulin Associates with β-Amyloid Peptide and Prevents Fibril Formation," Proc Natl Acad Sci USA (1998), 95:3275-80.
Iversen, et al., "The toxicity in vitro of β-amyloid protein," Biochem J (1995), 311( Pt 1):1-16.
Klunk, et al., "Quantifying Amyloid-Peptide (A) Aggregation Using the Congo Red-A (CR-A) Spectrophotometric Assay," Anal Biochem (1999), 266:66-76.
Lambert, et al., "Diffusible, Nonfibrillar Ligands Derived From aβ1-42 are Potent Central Nervous System Neurotoxins," Proc Nati Acad Sci USA (1998), 95:6448-53.
Liang, J. J. "Interaction between β-amyloid and lens βB-crystallin," (2000) FEBS Lett (2000), 484:98-101.
Macrae, T. H. "Structure and function of small heat shock/a-crystallin proteins: established concepts and emerging ideas," (2000) Cell Mol Life Sci (2000), 57:899-913.
McHaourab, et al., "Mechanism of Chaperone Function in Small Heat Shock Proteins," J Biol Chem (2002), 277:40557-66.
Norimine, et al., "Conservation of Babesia bovis Small Heat Shock Protein (Hsp20) among Strains and Definition of T Helper Cells Epitopes Recognized by Cattle with Diverse Major Histocompatibility Complex Class II Haplotypes," Infection and Immunity (2004), 72(2):1096-1106.
Pallitto, et al., "Recognition Sequence Design for Peptidyl Modulators of β-Amyloid Aggregation and Toxicity," Biochemistry (1999), 38:3570-8.
Pallitto, et al., "A Mathematical Model of the Kinetics of β-Amyloid Fibril Growth from the Denatured State," Biophys J (2001), 81:1805-22.
Renkawek, et al., "Dementia, Gliosis and expression of the Small Heat Shock Proteins hsp27 and Alpha B-crystallin in Parkinson's disease," Neuroreport (1999), 10:2273-2276.
Soto, et al., "β-sheet breaker peptides inhibit fibrillogenesis in a rat brain model of amyloidosis: Implications for Alzheimer's," Nat Med (1998), 4:822-6.
Stege, et al., "The Molecular Chaparone αB-crystallin Enhances Amyloid β Neurotoxicity," Biochem Biophys Res Commun (1999), 262:152-6.
Van Den Ijssel, et al., "Molecular chaperones: small heat shock proteins in the limelight," (1999) Curr Biol (1999), 9:R103-5.
Van Montfort, et al., "Crystal structure and assembly of a eukaryotic small heat shock protein," (2001) Nat Struct Biol (2001), 8:1025-30.
Wang, et al., "Development of a novel diffusion-based method to estimate the size of the aggregated Aβ species responsible for neurotoxicity," Biotechnol Bioeng (2002), 80:50-9.
Ward, et al., "Fractionation and characterization of oligomeric, protofibrillar and fibrillar forms of β-amyloid peptide," (2000) Biochem J (2000), 348(Pt 1):137-44.
Yong, et al., "Structure determination of micelle-like intermediates in amyloid β-protein fibril assembly by using small angle neutron scattering," (2002) Proc Natl Acad Sci USA (2002), 99:150-4.
United States Patent & Trademark Office, International Search Report and Written Opinion of the International Searching Authority for PCT/US2005/019020 dated Jun. 13, 2006, 11 pages.
Lee, et al. "Investigation of the Mechanism of Small Heat Shock Protein β-Amyloid Fibril Formation and Toxicity Prevention" Biophysical Journal 86 (1) p540a, Jan. 2004.
Garcia-Ranae, et al., "p23 and HSP20/α-crystallin proteins define a conserved sequence domain present in other eukaryotic protein families" FEBS Letters 529 (2002) 162-167, Sep. 16, 2002.
Kappe, et al., "The human genome encodes 10 α-crystallin-related small heat shock proteins: HspB1-10" Cell Stress & Chaperones (2003) 8 (1), 53-61.
Lee, et al., "Use of a novel alpha-crystalline to prevent beta-amyloid aggregation and toxicity" Biophysical Journal 84 (2 part 2); p. 154a Abstract presented at 47th Annual Meeting of the Biophysical Society, Mar. 1-5, 2003.
Kudva, et al., "Smal heat shock proteins inhibit in vitro Aβ1-42 amyloidogenesis" FEBS Letters 416 (1997) 117-121.
Ghanta, et al. "A Strategy for Designing Inhibitors of β-Amyloid Toxicity" (Nov. 22, 1996) J Biol Chem 271, 29525-8.
Tjernberg, et al., "Arrest of β-Amyloid Fibril Formation by a Pentapeptide Ligand" J Biol Chem 271, No. 15, Apr. 12, 1996, pp. 8545-8548.
Jakob, et al., "Small Heat Shock Proteins are Molecular Chaperones" J Biol Chem 268, No. 3, Jan. 25, 1993, pp. 1517-1520.
Horwitz, Joseph, "Alpha-crystallin can function as a molecular chaperone" Proc Natl Acad Sci USA 89, Nov. 1992, pp. 10449-10453.
Lomakin, et al., "Kinetic theory of fibrillogenesis of amyloid β-protein" Proc Natl Acad Sci USA vol. 94, pp. 7942-7947, Jul. 1997.

\* cited by examiner

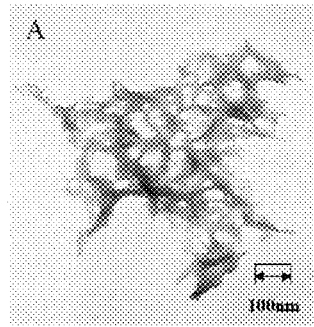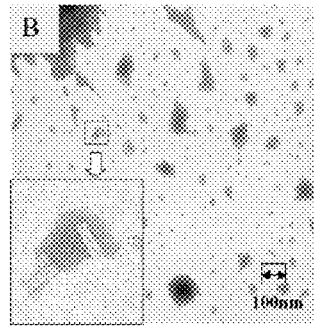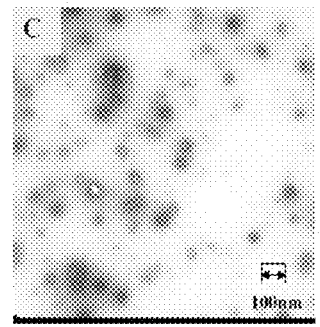
Figure 5A    Figure 5B    Figure 5C
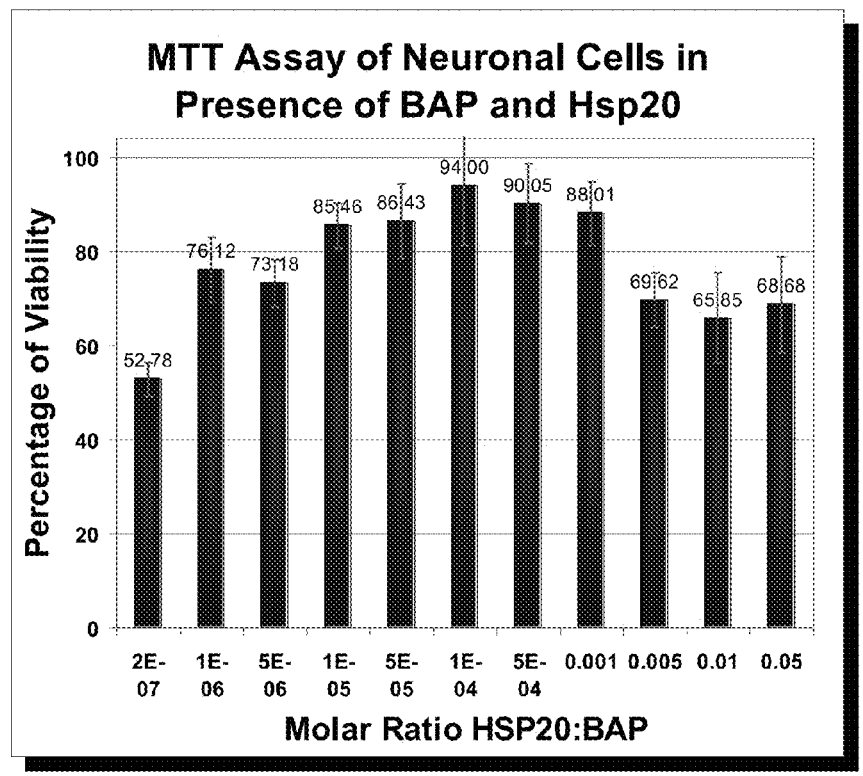
Figure 6

ATGGGGGGTTCTCATCATCATCATCATCATGGTATGGCTAGCATGACTGGTGGAC
AGCAAATGGGTCGGGATCTGTACGACGATGACGATAAGGATCCAACCCTTGAAA
ATCTTTATTTTCAAGGTATGTCGTGCATTATGAGGTGCAACAACTCCGAACAGGA
GGTTGTCATCGATGAGCAGACGGGACTCCCAGTGAAGAACCACGACTACACTGA
GAAGCCCTCTGTGATTTACAAGCCGTCGACCATTGTTCCTCAAAACACCATCCTT
GAGATCCCTCCTCCCAAGGAACTGGAAACCCCTATCACCTTCAACCCCACCGTC
GACACCTTTTTCGATGCTGACACCAACAAGATCGTTGTTTTGATGGAACTGCCTG
GATTCAGCCACAACGACATCACTGTGGAGTGCGGTTTGGGAGAACTCATCATCA
GCGGCCCCCGCCCCAAGGACGAGCTTTACGAGAAGTTCGGTAACAACCTTGACA
TCCACATCCGTGAGCGCAAGGTTGGTTACTTCTACAGGCGCTTCAAGCTCCCGC
ACAACGCCTTGGACAAGTCTGTTGCTGTGTCTTACTCCAACGGTATCTTGGACAT
CAGGATTGAGTGCTCGCAGTTCTCCGAGATGCGCCGCATCCAGATCGACGGCAA
GGCATAA

Figure 8

MGGSHHHHHHGMASMTGGQQMGRDLYDDDDKDPTLENLYFQGMSCIMRCNNSE
QEVVIDEQTGLPVKNHDYTEKPSVIYKPSTIVPQNTILEIPPPKELETPITFNPTVDTFF
DADTNKIVVLMELPGFSHNDITVECGLGELIISGPRPKDELYEKFGNNLDIHIRERKVG
YFYRRFKLPHNALDKSVAVSYSNGILDIRIECSQFSEMRRIQIDGKA

Figure 9

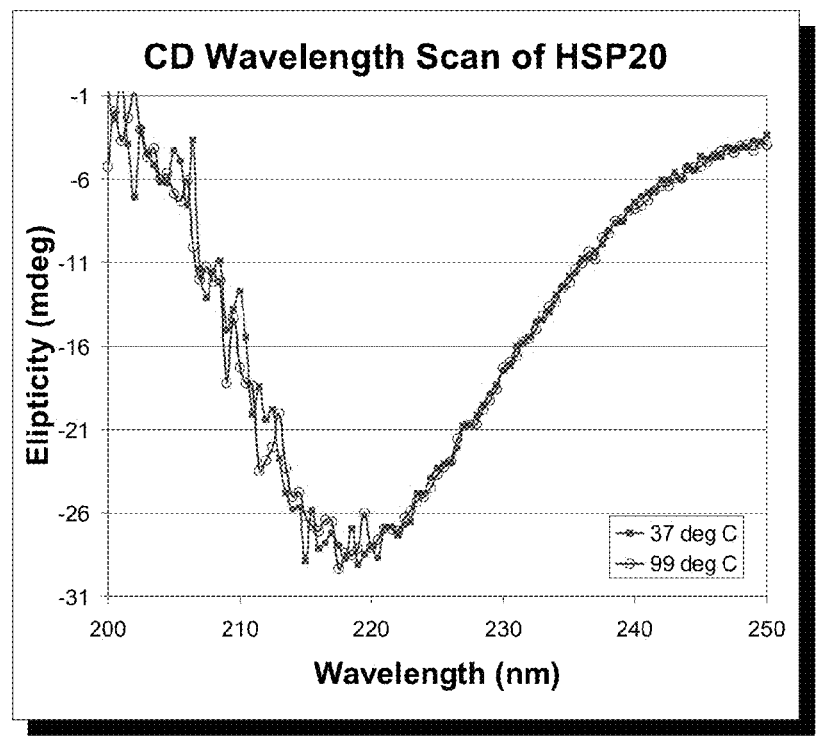
Figure 11
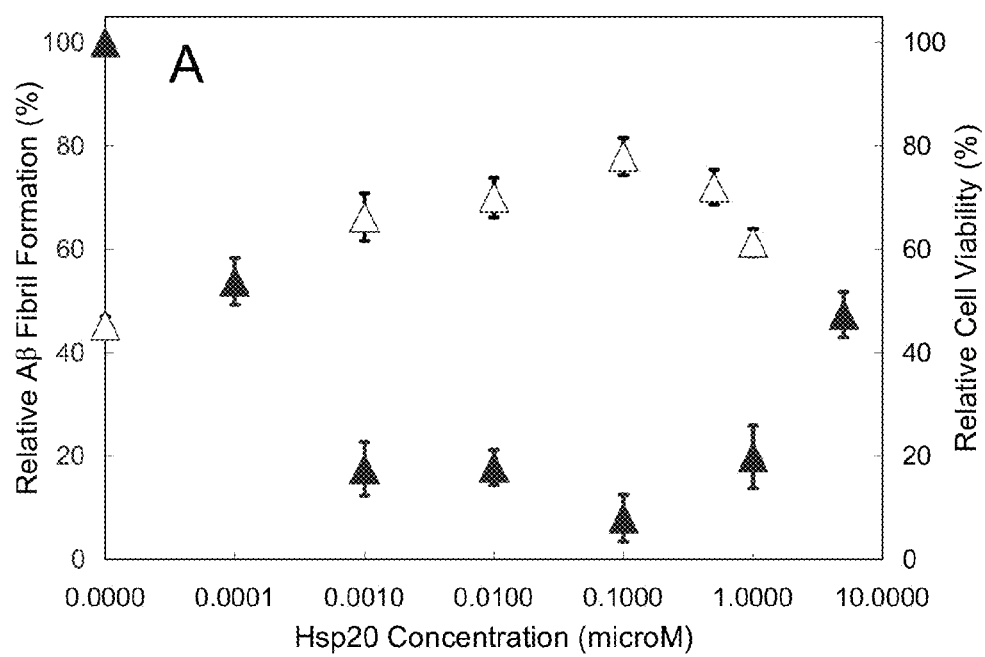
Figure 12A β

FIGURE 15
FIGURE 16
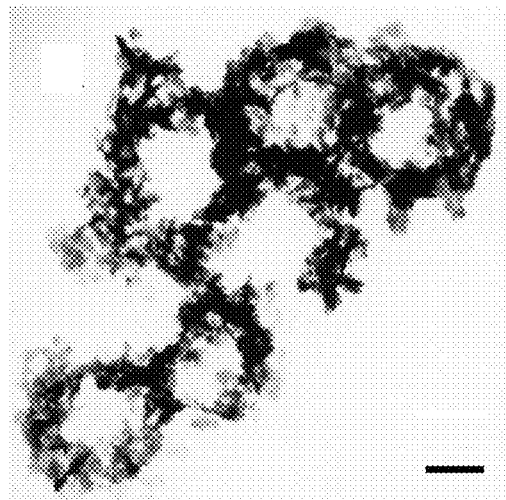
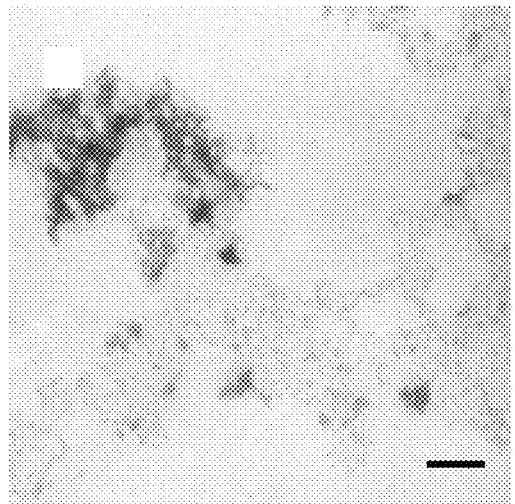
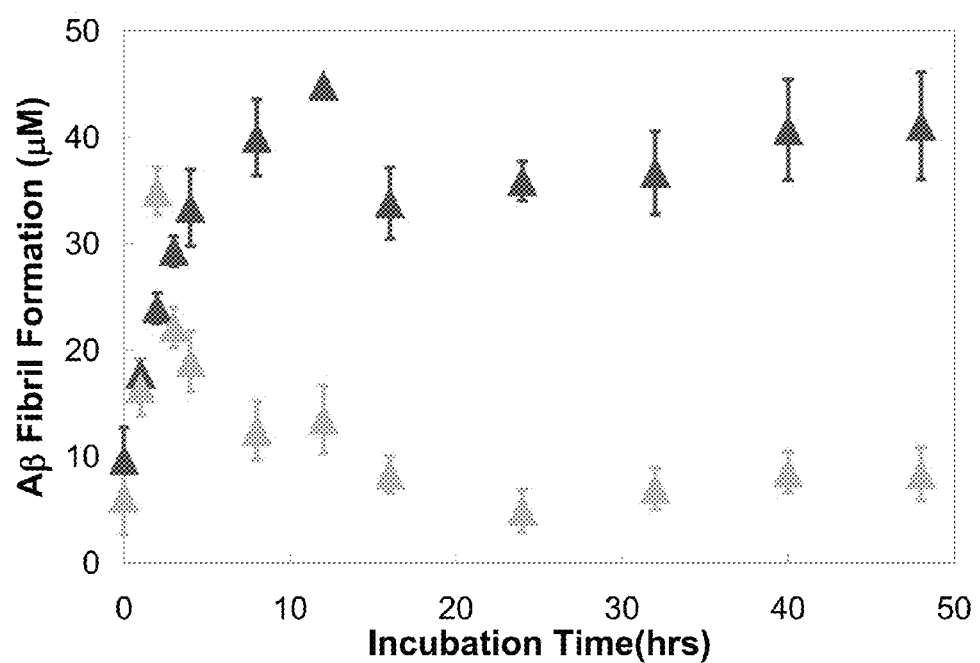
FIGURE 17

```
mjannaschiishp    1              MFGRDPFDSLFERMFKEFFATPMTGTTMIQSSTGIQ  36
BBovHSP20aa       1  MSCIMRCNNADQEVIIDEQTGLPIKSHDYSEKPSVIYKPSTTVPQNTLLE  50
                         .    . . *.    .  .*.   *  ..

mjannaschiishp   37  ISG-K------GFMPISIIEGDQ---HIKVIAWLPGVNKEDIILNAVGDT  76
BBovHSP20aa      51  IPPPKELENPITFNPTVDTFFDADNNKLVLLMELPGFSSTDINVECGWGE 100
                     *   *      * *         *    .. .. ***    **. .

mjannaschiishp   77  LEIRAKRSPLMITESE-RIIYSEIPEE--EEIYRTIKLPATVKEENASAK 123
BBovHSP20aa     101  LIISGPRNKDELYEKFGNNLDIHIRERKVGYFYRRFKLPNNAIDKSISVG 150
                     * *  *   .  *        .  * *       *  .   .  * mjannaschiishp  124  FENGVLSVILPKAESSIKKGINIE       147
BBovHSP20aa     151  YSNGILDIRIECSQFSEMRRVQIDAKA*   178
                     . **.*. .  .. *   ...*.
```

FIGURE 20

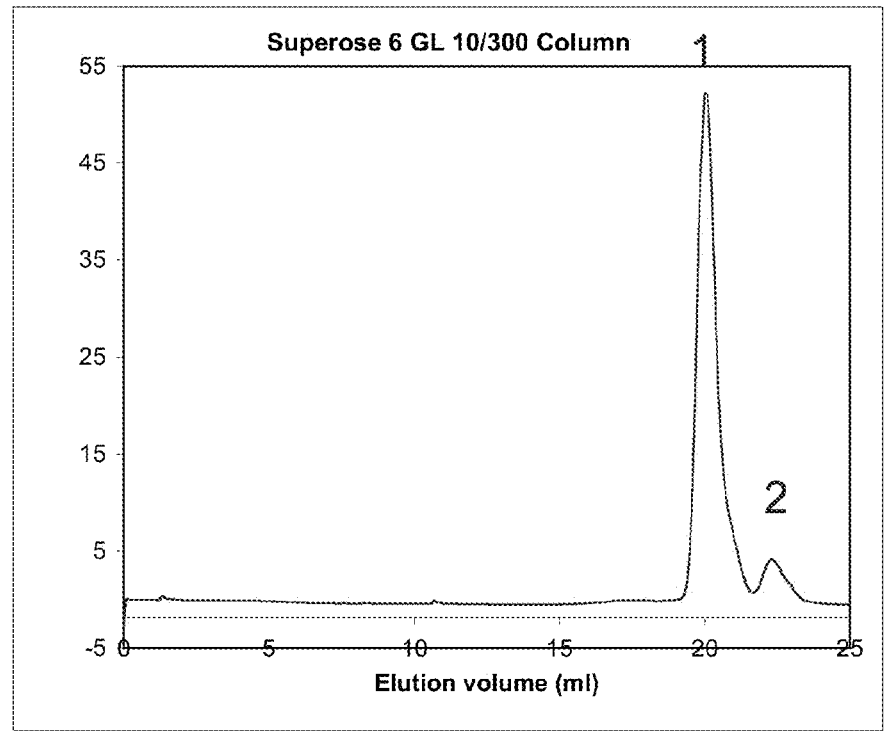

Figure 21

```
  1 MSCIMRCNNADQEVIIDEQTGLPIKSHDYSEKPSVIYKPSTTVPQNTLLE  50
 51 IPPPKELENPITFNPTVDTFFDADNNKLVLLMELPGFSSTDINVECGWGE 100
101 LIISGPRNKDELYEKFGNNLDIHIRERKVGYFYRRFKLPNNAIDKSISVG 150
151 YSNGILDIRIECSQFSEMRRVQIDAKA 178

1 IPPPKELENPITFNPTVDTFFDADNNKLVLLMELPGFSSTDINVECGWGE  50
 51 LIISGPRNKDELYEKFGNNLDIHIRERKVGYFYRRFKLPNNAIDKSISVG 100
101 YSNGILDIRIECSQFSEMRRVQIDAKA

1 MSCIMRCNNADQEVIIDEQTGLPIKSHDYSEKPSVIYKPSTTVPQNTLLE  50
 51 IPPPKELENPITFNPTVDTFFDADNNKLVLLMELPGFSSTDINVECGWGE 100
101 LIISGPRNKDELYEKFGNNLDIHIRERKVGYFYRRFKLPNNAIDKSISVG 150
151 YSNGILDIRIECSQFS

1 IPPPKELENPITFNPTVDTFFDADNNKLVLLMELPGFSSTDINVECGWGE  50
 51 LIISGPRNKDELYEKFGNNLDIHIRERKVGYFYRRFKLPNNAIDKSISVG 100
101 YSNGILDIRIECSQFS

-42 MGGSHHHHHHGMASMTGGQQMGRDLYDDDDKDPTLENLYFQG   His Tag
  1 MSCIMRCNNADQEVIIDEQTGLPIKSHDYSEKPSVIYKPSTTVPQNTLLE  50
 51 IPPPKELENPITFNPTVDTFFDADNNKLVLLMELPGFSSTDINVECGWGE 100
101 LIISGPRNKDELYEKFGNNLDIHIRERKVGYFYRRFKLPNNAIDKSISVG 150
151 YSNGILDIRIECSQFSEMRRVQIDAKA 178

-42 MGGSHHHHHHGMASMTGGQQMGRDLYDDDDKDPTLENLYFQG   His Tag
  1 IPPPKELENPITFNPTVDTFFDADNNKLVLLMELPGFSSTDINVECGWGE  50
 51 LIISGPRNKDELYEKFGNNLDIHIRERKVGYFYRRFKLPNNAIDKSISVG 100
101 YSNGILDIRIECSQFSEMRRVQIDAKA

-42 MGGSHHHHHHGMASMTGGQQMGRDLYDDDDKDPTLENLYFQG   His Tag
  1 MSCIMRCNNADQEVIIDEQTGLPIKSHDYSEKPSVIYKPSTTVPQNTLLE  50
 51 IPPPKELENPITFNPTVDTFFDADNNKLVLLMELPGFSSTDINVECGWGE 100
101 LIISGPRNKDELYEKFGNNLDIHIRERKVGYFYRRFKLPNNAIDKSISVG 150
151 YSNGILDIRIECSQFS

-42 MGGSHHHHHHGMASMTGGQQMGRDLYDDDDKDPTLENLYFQG   His Tag
  1 IPPPKELENPITFNPTVDTFFDADNNKLVLLMELPGFSSTDINVECGWGE  50
 51 LIISGPRNKDELYEKFGNNLDIHIRERKVGYFYRRFKLPNNAIDKSISVG 100
101 YSNGILDIRIECSQFS
```

Figure 24

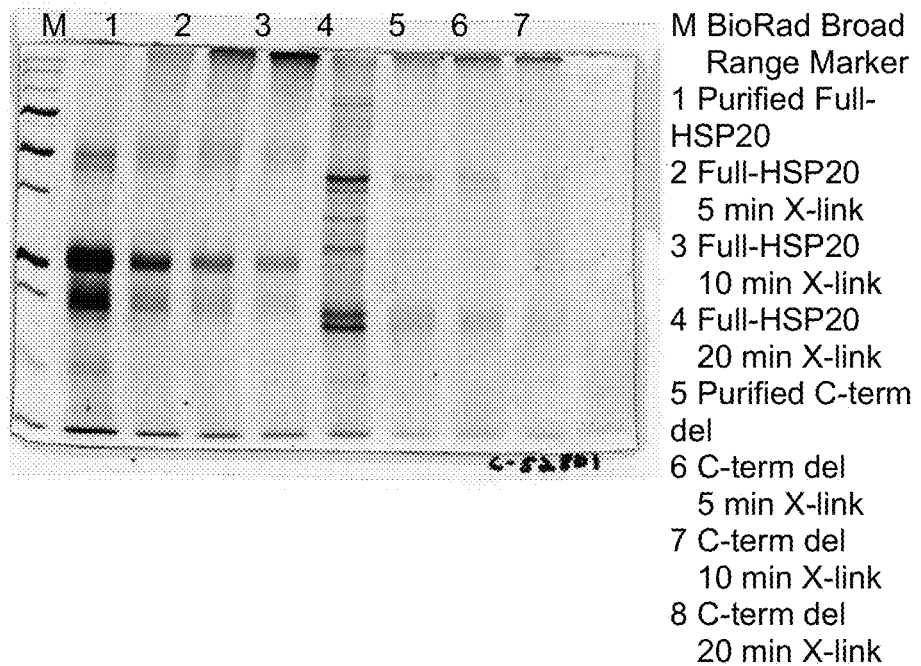

M BioRad Broad Range Marker
1 Purified Full-HSP20
2 Full-HSP20 5 min X-link
3 Full-HSP20 10 min X-link
4 Full-HSP20 20 min X-link
5 Purified C-term del
6 C-term del 5 min X-link
7 C-term del 10 min X-link
8 C-term del 20 min X-link

Figure 25

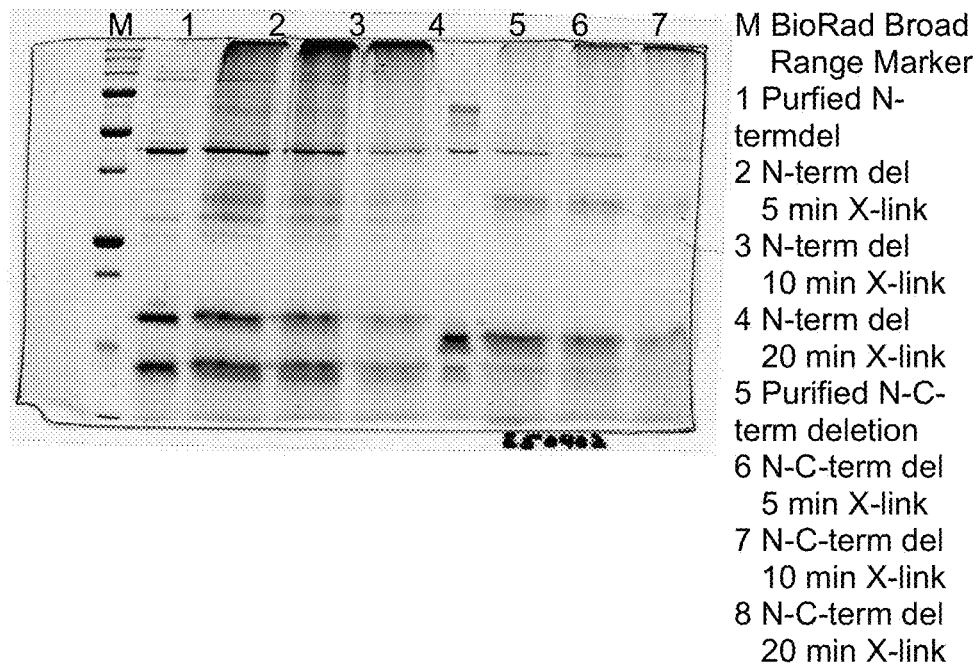

M BioRad Broad Range Marker
1 Purfied N-termdel
2 N-term del 5 min X-link
3 N-term del 10 min X-link
4 N-term del 20 min X-link
5 Purified N-C-term deletion
6 N-C-term del 5 min X-link
7 N-C-term del 10 min X-link
8 N-C-term del 20 min X-link

Figure 26

SEQUENCE LISTING

```
<160> NUMBER OF SEQ ID NOS: 20

<210> SEQ ID NO 1
<211> LENGTH: 660
<212> TYPE: DNA
<213> ORGANISM: Artificial Sequence
<220> FEATURE:
<223> OTHER INFORMATION: Synthetic primer

<400> SEQUENCE: 1 atgggggtt   ctcatcatca   tcatcatcat   ggtatggcta   gcatgactgg   tggacagcaa     60
atgggtcggg  atctgtacga  cgatgacgat   aaggatccaa   cccttgaaaa   tctttatttt    120
caaggtatgt  cgtgcattat   gaggtgcaac   aactccgaac   aggaggttgt   catcgatgag    180
cagacgggac  tcccagtgaa   gaaccacgac  tacactgaga   agccctctgt   gatttacaag    240
ccgtcgacca  ttgttcctca   aaacaccatc   cttgagatcc   ctcctcccaa   ggaactggaa    300
acccctatca  ccttcaaccc   caccgtcgac  acctttttcg   atgctgacac   caacaagatc    360
gttgttttga  tggaactgcc  tggattcagc   cacaacgaca   tcactgtgga   gtgcggtttg    420
ggagaactca  tcatcagcgg   cccccgcccc  aaggacgagc   tttacgagaa   gttcggtaac    480
aaccttgaca  tccacatccg   tgagcgcaag   gttggttact  tctacaggcg   cttcaagctc    540
ccgcacaacg  ccttggacaa   gtctgttgct   gtgtcttact   ccaacggtat   cttggacatc    600
aggattgagt  gctcgcagtt  ctccgagatg   cgccgcatcc   agatcgacgg   caaggcataa    660

<210> SEQ ID NO 2
<211> LENGTH: 219
<212> TYPE: PRT
<213> ORGANISM: Artificial Sequence
<220> FEATURE:
<223> OTHER INFORMATION: Synthetic peptide

<400> SEQUENCE: 2

Met Gly Gly Ser His His His His His His Gly Met Ala Ser Met Thr
1               5                   10                  15
```

```
Gly Gly Gln Gln Met Gly Arg Asp Leu Tyr Asp Asp Asp Lys Asp
            20                  25                  30

Pro Thr Leu Glu Asn Leu Tyr Phe Gln Gly Met Ser Cys Ile Met Arg
        35                  40                  45

Cys Asn Asn Ser Glu Gln Glu Val Val Ile Asp Glu Gln Thr Gly Leu
 50                  55                  60

Pro Val Lys Asn His Asp Tyr Thr Glu Lys Pro Ser Val Ile Tyr Lys
 65                  70                  75                  80

Pro Ser Thr Ile Val Pro Gln Asn Thr Ile Leu Glu Ile Pro Pro Pro
                85                  90                  95

Lys Glu Leu Glu Thr Pro Ile Thr Phe Asn Pro Thr Val Asp Thr Phe
            100                 105                 110

Phe Asp Ala Asp Thr Asn Lys Ile Val Val Leu Met Glu Leu Pro Gly
        115                 120                 125

Phe Ser His Asn Asp Ile Thr Val Glu Cys Gly Leu Gly Glu Leu Ile
 130                 135                 140

Ile Ser Gly Pro Arg Pro Lys Asp Glu Leu Tyr Glu Lys Phe Gly Asn
145                 150                 155                 160

Asn Leu Asp Ile His Ile Arg Glu Arg Lys Val Gly Tyr Phe Tyr Arg
                165                 170                 175

Arg Phe Lys Leu Pro His Asn Ala Leu Asp Lys Ser Val Ala Val Ser
            180                 185                 190

Tyr Ser Asn Gly Ile Leu Asp Ile Arg Ile Glu Cys Ser Gln Phe Ser
        195                 200                 205

Glu Met Arg Arg Ile Gln Ile Asp Gly Lys Ala
    210                 215

<210> SEQ ID NO 3
<211> LENGTH: 42
<212> TYPE: DNA
<213> ORGANISM: Artificial Sequence
<220> FEATURE:
<223> OTHER INFORMATION: Synthetic primer

<400> SEQUENCE: 3
gaaaatcttt attttcaagg tatgtcgtgt attatgaggt gc                          42

<210> SEQ ID NO 4
<211> LENGTH: 27
<212> TYPE: DNA
<213> ORGANISM: Artificial Sequence
<220> FEATURE:
<223> OTHER INFORMATION: Synthetic primer

<400> SEQUENCE: 4
ctattaggcc ttggcgtcaa tctgaac                                           27

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Glu Met Arg Arg Val Gln Ile Asp Ala Lys Ala
  1               5                  10

<210> SEQ ID NO 6
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 6

Lys Leu Val Phe Phe
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Leu Pro Phe Phe Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Gly Val Val Ile Asn
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide

<400> SEQUENCE: 9

Arg Val Val Ile Ala
1               5

<210> SEQ ID NO 10
<211> LENGTH: 177
<212> TYPE: PRT
<213> ORGANISM: Artificial Sequence
<220> FEATURE:
<223> OTHER INFORMATION: Synthetic peptide

<400> SEQUENCE: 10

Cys Glu Glu Glu Glu Cys Cys Cys Cys Cys Glu Glu Glu Glu Glu
1               5                   10                  15

Cys Cys Cys Cys Cys Cys Cys Cys Cys Cys Cys Cys Cys Cys Cys
                20                  25                  30

Cys Cys Cys Cys Cys Cys Cys Cys Cys Cys Cys His His His His
            35                  40                  45

His His Cys Cys Cys His His His Cys Cys Cys Cys Cys Cys Cys
        50                  55                  60

Cys Cys Cys Cys Cys Glu Glu Cys Cys Cys Cys Glu Glu Glu Glu
65                  70                  75                  80

Glu Glu Glu Cys Cys Cys Cys Cys His His His Glu Glu Glu Glu
                85                  90                  95

Glu Cys Cys Glu Glu Glu Glu Glu Glu Glu Cys Cys Cys Cys Cys
                100                 105                 110
```

```
Cys Cys Cys Cys Cys Cys Cys Cys Glu Glu Glu Glu Glu Glu
        115                 120                 125

Glu Cys Glu Glu Glu Glu Glu Glu Cys Cys Cys Cys Cys His
    130                 135                 140

His His Glu Glu Glu Glu Glu Cys Cys Glu Glu Glu Glu Glu
145                 150                 155                 160

Glu Cys Cys Cys Cys Cys Cys Glu Glu Glu Glu Glu Glu Cys
            165                 170                 175

Cys
```

<210> SEQ ID NO 11
<211> LENGTH: 176
<212> TYPE: PRT
<213> ORGANISM: Artificial Sequence
<220> FEATURE:
<223> OTHER INFORMATION: Synthetic peptide

<400> SEQUENCE: 11

```
Met Ser Cys Ile Met Arg Cys Asn Asn Ala Asp Gln Glu Val Ile Ile
1               5                   10                  15

Asp Glu Gln Thr Gly Leu Pro Ile Lys Ser His Asp Tyr Ser Glu Lys
            20                  25                  30

Pro Ser Val Ile Tyr Lys Pro Ser Thr Thr Val Pro Gln Asn Thr Leu
        35                  40                  45

Leu Glu Ile Pro Pro Lys Glu Leu Glu Asn Pro Ile Thr Phe Asn
    50                  55                  60

Pro Thr Val Asp Thr Phe Phe Asp Ala Asp Asn Lys Leu Val Leu
65                  70                  75                  80

Leu Met Glu Leu Pro Gly Phe Ser Ser Thr Asp Ile Asn Val Glu Cys
                85                  90                  95

Gly Trp Gly Leu Ile Ile Ser Gly Pro Arg Asn Lys Asp Glu Leu Tyr
            100                 105                 110

Glu Lys Phe Gly Asn Asn Leu Asp Ile His Ile Arg Glu Arg Lys Val
        115                 120                 125

Gly Tyr Phe Tyr Arg Arg Phe Lys Leu Pro Asn Asn Ala Ile Asp Lys
    130                 135                 140

Ser Ile Ser Val Gly Tyr Ser Asn Gly Ile Leu Asp Ile Arg Ile Glu
145                 150                 155                 160

Cys Ser Gln Phe Ser Glu Met Arg Arg Val Gln Ile Asp Ala Lys Ala
                165                 170                 175
```

<210> SEQ ID NO 12
<211> LENGTH: 147
<212> TYPE: PRT
<213> ORGANISM: Artificial Sequence
<220> FEATURE:
<223> OTHER INFORMATION: Synthetic peptide

<400> SEQUENCE: 12

```
Met Phe Gly Arg Asp Pro Phe Asp Ser Leu Phe Glu Arg Met Phe Lys
1               5                   10                  15

Glu Phe Phe Ala Thr Pro Met Thr Gly Thr Thr Met Ile Gln Ser Ser
            20                  25                  30

Thr Gly Ile Gln Ile Ser Gly Lys Gly Phe Met Pro Ile Ser Ile Ile
        35                  40                  45

Glu Gly Asp Gln His Ile Lys Val Ile Ala Trp Leu Pro Gly Val Asn
    50                  55                  60
```

Lys Glu Asp Ile Ile Leu Asn Ala Val Gly Asp Thr Leu Glu Ile Arg
65                  70                  75                  80

Ala Lys Arg Ser Pro Leu Met Ile Thr Glu Ser Glu Arg Ile Ile Tyr
                85                  90                  95

Ser Glu Ile Pro Glu Glu Glu Ile Tyr Arg Thr Ile Lys Leu Pro
            100                 105                 110

Ala Thr Val Lys Glu Glu Asn Ala Ser Ala Lys Phe Glu Asn Gly Val
            115                 120                 125

Leu Ser Val Ile Leu Pro Lys Ala Glu Ser Ser Ile Lys Lys Gly Ile
        130                 135                 140

Asn Ile Glu
145

<210> SEQ ID NO 13
<211> LENGTH: 177
<212> TYPE: PRT
<213> ORGANISM: Artificial Sequence
<220> FEATURE:
<223> OTHER INFORMATION: Synthetic peptide

<400> SEQUENCE: 13

Met Ser Cys Ile Met Arg Cys Asn Asn Ala Asp Gln Glu Val Ile Ile
1               5                   10                  15

Asp Glu Gln Thr Gly Leu Pro Ile Lys Ser His Asp Tyr Ser Glu Lys
            20                  25                  30

Pro Ser Val Ile Tyr Lys Pro Ser Thr Thr Val Pro Gln Asn Thr Leu
        35                  40                  45

Leu Glu Ile Pro Pro Lys Glu Leu Glu Asn Pro Ile Thr Phe Asn
    50                  55                  60

Pro Thr Val Asp Thr Phe Phe Asp Ala Asp Asn Asn Lys Leu Val Leu
65                  70                  75                  80

Leu Met Glu Leu Pro Gly Phe Ser Ser Thr Asp Ile Asn Val Glu Cys
                85                  90                  95

Gly Trp Gly Glu Leu Ile Ile Ser Gly Pro Arg Asn Lys Asp Glu Leu
            100                 105                 110

Tyr Glu Lys Phe Gly Asn Asn Leu Asp Ile His Ile Arg Glu Arg Lys
        115                 120                 125

Val Gly Tyr Phe Tyr Arg Arg Phe Lys Leu Pro Asn Asn Ala Ile Asp
    130                 135                 140

Lys Ser Ile Ser Val Gly Tyr Ser Asn Gly Ile Leu Asp Ile Arg Ile
145                 150                 155                 160

Glu Cys Ser Gln Phe Ser Glu Met Arg Arg Val Gln Ile Asp Ala Lys
                165                 170                 175

Ala

<210> SEQ ID NO 14
<211> LENGTH: 127
<212> TYPE: PRT
<213> ORGANISM: Artificial Sequence
<220> FEATURE:
<223> OTHER INFORMATION: Synthetic peptide

<400> SEQUENCE: 14

Ile Pro Pro Pro Lys Glu Leu Glu Asn Pro Ile Thr Phe Asn Pro Thr
1               5                   10                  15

Val Asp Thr Phe Phe Asp Ala Asp Asn Asn Lys Leu Val Leu Leu Met
            20                  25                  30

Glu Leu Pro Gly Phe Ser Ser Thr Asp Ile Asn Val Glu Cys Gly Trp
                35                  40                  45

Gly Glu Leu Ile Ile Ser Gly Pro Arg Asn Lys Asp Glu Leu Tyr Glu
            50                  55                  60

Lys Phe Gly Asn Asn Leu Asp Ile His Ile Arg Glu Arg Lys Val Gly
65                  70                  75                  80

Tyr Phe Tyr Arg Arg Phe Lys Leu Pro Asn Asn Ala Ile Asp Lys Ser
                85                  90                  95

Ile Ser Val Gly Tyr Ser Asn Gly Ile Leu Asp Ile Arg Ile Glu Cys
            100                 105                 110

Ser Gln Phe Ser Glu Met Arg Arg Val Gln Ile Asp Ala Lys Ala
                115                 120                 125

<210> SEQ ID NO 15
<211> LENGTH: 166
<212> TYPE: PRT
<213> ORGANISM: Artificial Sequence
<220> FEATURE:
<223> OTHER INFORMATION: Synthetic peptide

<400> SEQUENCE: 15

Met Ser Cys Ile Met Arg Cys Asn Asn Ala Asp Gln Glu Val Ile Ile
1               5                   10                  15

Asp Glu Gln Thr Gly Leu Pro Ile Lys Ser His Asp Tyr Ser Glu Lys
            20                  25                  30

Pro Ser Val Ile Tyr Lys Pro Ser Thr Thr Val Pro Gln Asn Thr Leu
                35                  40                  45

Leu Glu Ile Pro Pro Lys Glu Leu Glu Asn Pro Ile Thr Phe Asn
        50                  55                  60

Pro Thr Val Asp Thr Phe Phe Asp Ala Asp Asn Asn Lys Leu Val Leu
65                  70                  75                  80

Leu Met Glu Leu Pro Gly Phe Ser Ser Thr Asp Ile Asn Val Glu Cys
                85                  90                  95

Gly Trp Gly Glu Leu Ile Ile Ser Gly Pro Arg Asn Lys Asp Glu Leu
            100                 105                 110

Tyr Glu Lys Phe Gly Asn Asn Leu Asp Ile His Ile Arg Glu Arg Lys
        115                 120                 125

Val Gly Tyr Phe Tyr Arg Arg Phe Lys Leu Pro Asn Asn Ala Ile Asp
    130                 135                 140

Lys Ser Ile Ser Val Gly Tyr Ser Asn Gly Ile Leu Asp Ile Arg Ile
145                 150                 155                 160

Glu Cys Ser Gln Phe Ser
                165

<210> SEQ ID NO 16
<211> LENGTH: 116
<212> TYPE: PRT
<213> ORGANISM: Artificial Sequence
<220> FEATURE:
<223> OTHER INFORMATION: Synthetic peptide

<400> SEQUENCE: 16

Ile Pro Pro Lys Glu Leu Glu Asn Pro Ile Thr Phe Asn Pro Thr
1               5                   10                  15

Val Asp Thr Phe Phe Asp Ala Asp Asn Asn Lys Leu Val Leu Leu Met
            20                  25                  30

Glu Leu Pro Gly Phe Ser Ser Thr Asp Ile Asn Val Glu Cys Gly Trp

```
                    35                  40                  45
Gly Glu Leu Ile Ile Ser Gly Pro Arg Asn Lys Asp Glu Leu Tyr Glu
                50                  55                  60

Lys Phe Gly Asn Asn Leu Asp Ile His Ile Arg Glu Arg Lys Val Gly
 65                  70                  75                  80

Tyr Phe Tyr Arg Arg Phe Lys Leu Pro Asn Asn Ala Ile Asp Lys Ser
                    85                  90                  95

Ile Ser Val Gly Tyr Ser Asn Gly Ile Leu Asp Ile Arg Ile Glu Cys
                100                 105                 110

Ser Gln Phe Ser
            115

<210> SEQ ID NO 17
<211> LENGTH: 219
<212> TYPE: PRT
<213> ORGANISM: Artificial Sequence
<220> FEATURE:
<223> OTHER INFORMATION: Synthetic peptide

<400> SEQUENCE: 17

Met Gly Gly Ser His His His His His His Gly Met Ala Ser Met Thr
  1               5                  10                  15

Gly Gly Gln Gln Met Gly Arg Asp Leu Tyr Asp Asp Asp Lys Asp
                20                  25                  30

Pro Thr Leu Glu Asn Leu Tyr Phe Gln Gly Met Ser Cys Ile Met Arg
            35                  40                  45

Cys Asn Asn Ala Asp Gln Glu Val Ile Ile Asp Glu Gln Thr Gly Leu
         50                  55                  60

Pro Ile Lys Ser His Asp Tyr Ser Glu Lys Pro Ser Val Ile Tyr Lys
 65                  70                  75                  80

Pro Ser Thr Thr Val Pro Gln Asn Thr Leu Leu Glu Ile Pro Pro Pro
                    85                  90                  95

Lys Glu Leu Glu Asn Pro Ile Thr Phe Asn Pro Thr Val Asp Thr Phe
                100                 105                 110

Phe Asp Ala Asp Asn Asn Lys Leu Val Leu Leu Met Glu Leu Pro Gly
            115                 120                 125

Phe Ser Ser Thr Asp Ile Asn Val Glu Cys Gly Trp Gly Glu Leu Ile
130                 135                 140

Ile Ser Gly Pro Arg Asn Lys Asp Glu Leu Tyr Glu Lys Phe Gly Asn
145                 150                 155                 160

Asn Leu Asp Ile His Ile Arg Glu Arg Lys Val Gly Tyr Phe Tyr Arg
                165                 170                 175

Arg Phe Lys Leu Pro Asn Asn Ala Ile Asp Lys Ser Ile Ser Val Gly
                180                 185                 190

Tyr Ser Asn Gly Ile Leu Asp Ile Arg Ile Glu Cys Ser Gln Phe Ser
            195                 200                 205

Glu Met Arg Arg Val Gln Ile Asp Ala Lys Ala
        210                 215

<210> SEQ ID NO 18
<211> LENGTH: 169
<212> TYPE: PRT
<213> ORGANISM: Artificial Sequence
<220> FEATURE:
<223> OTHER INFORMATION: Synthetic peptide

<400> SEQUENCE: 18
```

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Pro Thr Leu Glu Asn Leu Tyr Phe Gln Gly Ile Pro Pro Lys Glu
                35                  40                  45

Leu Glu Asn Pro Ile Thr Phe Asn Pro Thr Val Asp Thr Phe Asp
 50                  55                  60

Ala Asp Asn Asn Lys Leu Val Leu Leu Met Glu Leu Pro Gly Phe Ser
 65                  70                  75                  80

Ser Thr Asp Ile Asn Val Glu Cys Gly Trp Gly Glu Leu Ile Ile Ser
                85                  90                  95

Gly Pro Arg Asn Lys Asp Glu Leu Tyr Glu Lys Phe Gly Asn Asn Leu
                100                 105                 110

Asp Ile His Ile Arg Glu Arg Lys Val Gly Tyr Phe Tyr Arg Arg Phe
                115                 120                 125

Lys Leu Pro Asn Asn Ala Ile Asp Lys Ser Ile Ser Val Gly Tyr Ser
    130                 135                 140

Asn Gly Ile Leu Asp Ile Arg Ile Glu Cys Ser Gln Phe Ser Glu Met
145                 150                 155                 160

Arg Arg Val Gln Ile Asp Ala Lys Ala
                165
```

```
<210> SEQ ID NO 19
<211> LENGTH: 208
<212> TYPE: PRT
<213> ORGANISM: Artificial Sequence
<220> FEATURE:
<223> OTHER INFORMATION: Synthetic peptide

<400> SEQUENCE: 19
```

```
Met Gly Gly Ser His His His His His Gly Met Ala Ser Met Thr
 1               5                  10                  15

Gly Gly Gln Gln Met Gly Arg Asp Leu Tyr Asp Asp Asp Lys Asp
                20                  25                  30

Pro Thr Leu Glu Asn Leu Tyr Phe Gln Gly Met Ser Cys Ile Met Arg
                35                  40                  45

Cys Asn Asn Ala Asp Gln Glu Val Ile Ile Asp Glu Gln Thr Gly Leu
 50                  55                  60

Pro Ile Lys Ser His Asp Tyr Ser Glu Lys Pro Ser Val Ile Tyr Lys
 65                  70                  75                  80

Pro Ser Thr Thr Val Pro Gln Asn Thr Leu Glu Ile Pro Pro
                85                  90                  95

Lys Glu Leu Glu Asn Pro Ile Thr Phe Asn Pro Thr Val Asp Thr Phe
                100                 105                 110

Phe Asp Ala Asp Asn Asn Lys Leu Val Leu Leu Met Glu Leu Pro Gly
    115                 120                 125

Phe Ser Ser Thr Asp Ile Asn Val Glu Cys Gly Trp Gly Glu Leu Ile
    130                 135                 140

Ile Ser Gly Pro Arg Asn Lys Asp Glu Leu Tyr Glu Lys Phe Gly Asn
145                 150                 155                 160

Asn Leu Asp Ile His Ile Arg Glu Arg Lys Val Gly Tyr Phe Tyr Arg
                165                 170                 175

Arg Phe Lys Leu Pro Asn Asn Ala Ile Asp Lys Ser Ile Ser Val Gly
                180                 185                 190
```

-continued

```
Tyr Ser Asn Gly Ile Leu Asp Ile Arg Ile Glu Cys Ser Gln Phe Ser
        195                 200                 205

<210> SEQ ID NO 20
<211> LENGTH: 158
<212> TYPE: PRT
<213> ORGANISM: Artificial Sequence
<220> FEATURE:
<223> OTHER INFORMATION: Synthetic peptide

<400> SEQUENCE: 20

Met Gly Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Pro Thr Leu Glu Asn Leu Tyr Phe Gln Gly Ile Pro Pro Pro Lys Glu
        35                  40                  45

Leu Glu Asn Pro Ile Thr Phe Asn Pro Thr Val Asp Thr Phe Phe Asp
    50                  55                  60

Ala Asp Asn Asn Lys Leu Val Leu Leu Met Glu Leu Pro Gly Phe Ser
65                  70                  75                  80

Ser Thr Asp Ile Asn Val Glu Cys Gly Trp Gly Glu Leu Ile Ile Ser
                85                  90                  95

Gly Pro Arg Asn Lys Asp Glu Leu Tyr Glu Lys Phe Gly Asn Asn Leu
            100                 105                 110

Asp Ile His Ile Arg Glu Arg Lys Val Gly Tyr Phe Tyr Arg Arg Phe
        115                 120                 125

Lys Leu Pro Asn Asn Ala Ile Asp Lys Ser Ile Ser Val Gly Tyr Ser
    130                 135                 140

Asn Gly Ile Leu Asp Ile Arg Ile Glu Cys Ser Gln Phe Ser
145                 150                 155
```

HSP20 INHIBITS AMYLOIDOGENESIS AND NEUROTOXICITY

CROSS-REFERENCE TO RELATED APPLICATIONS

This patent application is a is a divisional patent application of U.S. Ser. No. 11/139,770 filed on May 26, 2005, which claims priority to U.S. provisional patent application 60/575,758 filed on May 26, 2004 and entitled "HSP20 Inhibits Amyloidogenesis and Neurotoxicity," all of which are hereby incorporated by reference in their entirety.

STATEMENT OF FEDERALLY FUNDED RESEARCH

The U.S. Government may own certain rights in this invention pursuant to the terms of the NSF Grant No. BES-9734496.

TECHNICAL FIELD OF THE INVENTION

The present invention relates in general to the field of amyloidogenesis, and more particularly, to a heat shock protein with β-pleated sheets that inhibits amyloidogenesis and neurotoxicity.

REFERENCE TO A SEQUENCE LISTING

The present application includes a Sequence Listing filed separately as required by 37 CFR 1.821-1.825.

BACKGROUND OF THE INVENTION

Without limiting the scope of the invention, its background is described in connection with amyloidogenesis and neurotoxicity.

A number of pathophysiologic diseases have been classified as involving "amyloidosis," which are characterized by the deposition of abnormal fibrils ("amyloid fibrils") in extracellular spaces. The amyloid fibril formation is thought to represent a final common result from the misfolding of a diverse array of proteins. Regardless of their biochemical composition, all types of amyloid fibrils share certain characteristics, including: a β-pleated sheet structure; green birefringence under polarized light after staining with Congo Red dye; and a fibrillar morphology in electron micrographs.

The deposition of amyloid fibrils affects several organs. One type of amyloid fibril causes "cerebral amyloidosis," which covers the Alzheimer group of diseases, namely, Alzheimer's disease (e.g., pre-senile dementia, senile dementia); Alzheimer's disease associated with Down's syndrome; Alzheimer's disease associated with other central-nervous-system diseases, such as Parkinson's disorder; and congophilic angiopathy (whether or not associated with Alzheimer's disease).

Presently, there is no effective therapy for cerebral amyloidosis, which was a fatal outcome following the onset of amyloid deposits. Alzheimer's disease (AD) is estimated to be the fourth or fifth leading cause of death among North Americans. Accumulating biochemical, histological, and genetic evidence supports the hypothesis that the 4 kDa β-amyloid protein (Aβ) is an essential component in the pathogenesis of Alzheimer's disease. Selkoe D J, Science 275:630-631 (1997); Hardy J, Proc Natl Acad Sci USA 94:2095-2097 (1997). Despite the intense interest in the role of Aβ in the etiology of AD, the role of Aβ in fibril formation is poorly understood.

SUMMARY OF THE INVENTION

The present inventors have recognized and discovered that Hsp20, a novel α-crystallin isolated from the bovine erythrocyte parasite *Babesia bovis*, is able to prevent aggregation of amyloidogenic proteins. It was found that the α-crystallin isolated and purified from the bovine erythrocyte parasite *Babesia bovis* was able to prevent amyloidogenic target proteins, e.g., β-Amyloid (Aβ), from aggregating when the Hsp20 and the target protein were at or near equimolar levels. It was further found that Hsp20 prevented Aβ amyloid formation at a wide range of molar ratios of Hsp20 to Aβ, e.g., of about 1:1,000 to 1:200,000. Surprisingly, at higher concentrations of Hsp20, the protein no longer displays its aggregation inhibition and toxicity attenuation properties. The development of novel aggregation inhibitors is useful for the treatment of neurodegenerative diseases and disorders, e.g., Alzheimer's, Huntington's, and Parkinson's disease and prion proteins, that involve amyloid toxicity.

More particularly, the present invention includes an isolated and purified polypeptide that includes a portion of an α-crystallin polypeptide having one or more β-pleated sheets that inhibits neurotoxicity and amyloidogenesis. For example, the polypeptide may be non-human, such as a polypeptide from a bovine erythrocyte parasite. One particular example of a used to prevent neurotoxicity and amyloidogenesis may be at least a portion of an Hsp20 polypeptide from a *Babesia* sp. bovine erythrocyte parasite, e.g., *Babesia bovis*. In one example, the present invention includes both the nucleic acid (SEQ ID NO.:1) and/or the amino acid sequences of the Hsp20 protein (SEQ ID NO.: 2), truncations and fusion proteins thereof. For example, the Hsp20 polypeptide may include a tag that permits rapid isolation, e.g., a His-tag and even a protease cleavage site, as are well-known to skilled artisans.

The present invention also includes a method of making an α-crystallin polypeptide by culturing a host cell into which a nucleic acid sequence encoding at least a portion of the polypeptide of SEQ ID NO.: 2 has been introduced in transient, selective or permanent form under conditions wherein the host cell expresses the polypeptide and wherein the polypeptide exhibits α-crystallin activity, attenuated neurotoxicity and inhibits amyloidogenesis. An isolated and purified polypeptide may be expressed and isolated by the methods disclosed herein.

One example of a protein for use with the present invention is an isolated and purified, small heat shock protein that includes one or more β-pleated sheets that modulates neurotoxicity over about a one-thousand-fold concentration range by stabilizing an amyloidogenic protein. The concentration range for the activity of the reduction in neurotoxicity of target protein is between about 1 nM to about 5 μM. In another example, the molar ratio of heat shock protein to amyloidogenic protein may be between about 0.0005 to about 0.001. These proteins may be used in a method of stabilizing a protein with one or more β-pleated sheet by contacting the protein with a heat shock polypeptide with one or more β-pleated sheets wherein the protein remains stable and exhibits attenuated neurotoxicity over a one-thousand-fold concentration range.

The present invention may also be used in a method for stabilizing a protein with a β-pleated sheet in which the target protein is contacted with a heat shock polypeptide that includes one or more β-pleated sheets wherein the protein remains stable over a one-thousand-fold concentration range at a high temperature. The heat shock polypeptide may be an Hsp20 that exhibits α-crystallin activity and inhibits the formation of Aβ multimers such as a parasitic, bacterial, viral, fungal or mammalian analog of Hsp20 that exhibits α-crystallin activity and attenuated toxicity to Aβ. The small, heat shock protein (and truncations thereof), may be used in a method of reducing protein aggregation by contacting an aggregation of proteins with an Hsp20 wherein the protein aggregation is reduced. The proteins of the present invention, either with or without a tag, may be used in, e.g., a method of treating a medical condition that exhibits protein aggregation by administering to a subject a physiological effective amount of a heat shock protein with one or more β-pleated sheets, whereby the protein reduces protein aggregation levels in a neuronal tissue of the subject.

The method of preventing protein aggregation disclosed herein includes contacting an amyloidogenic protein with an effective amount of at least a portion of the polypeptide of SEQ ID NO.: 2. The amyloidogenic protein may be in, at or about a tissue, e.g., in, at or about a neural cell. The protein for preventing aggregation includes an isolated and purified portion of a polypeptide having a significant similarity to the α-crystallin family of proteins and one or more β-pleated sheets isolated from *Babesia* sp., e.g., full-length Hsp20, or amino, carboxy, or amino and carboxy terminus truncated Hsp20 protein that inhibits, e.g., $A\beta_{1-40}$ fibril formation.

Yet another embodiment of the present invention is a kit or dosage form that includes a first container having an isolated or purified polypeptide with α-crystallin activity and one or more β-pleated sheets that inhibits neurotoxicity and amyloidogenesis. For example, a pharmaceutical composition for treating amyloidogenesis may include an effective amount of at least a portion of a purified polypeptide with α-crystallin activity and one or more β-pleated sheets that inhibits neurotoxicity and amyloidogenesis in pharmaceutically acceptable carrier. One such isolated and purified polypeptide includes an α-crystallin, small, heat shock protein Hsp20 having one or more β-pleated sheets that inhibits neurotoxicity and amyloidogenesis, e.g., one isolated and purified (from the organism or as a recombinant product) from a *Babesia bovis*. The polypeptide may also include a tag for isolation, e.g., an MBP, myc, GST, His-tag and the like.

BRIEF DESCRIPTION OF THE DRAWINGS

For a more complete understanding of the features and advantages of the present invention, reference is now made to the detailed description of the invention along with the accompanying figures and in which:

FIGS. 5A to 5C are electron micrographs of Aβ fibrils, Hsp20, and Aβ-Hsp20 mixtures, respectively;

FIG. 6 is a graph that plots cell viability as a function of Hsp20 concentration;

FIG. 8 is a nucleic acid sequence of an Hsp20 for use with the present invention (SEQ ID NO.: 1);

FIG. 9 is the amino acid sequence of an Hsp20 (SEQ ID NO: 2) for use with the present invention in accordance with SEQ ID NO: 1;

FIG. 11 is a graph of CD measurements carried out on an AVIV model 62;

FIGS. 12A to 12C show the activities of small heat shock proteins (sHsps) to prevent Aβ aggregation and toxicity. All protein samples containing Aβ and sHsps were mixed for 24 hours before aggregation and toxicity assay. Congo red was used as an indicator of Aβ aggregation and FACS array was used for the biological activities using dye. (12A) 100 μM Aβ with His-Hsp20 (solid triangles: Congo red assay, blank triangles: biological activities); (12B) 20 μM Aβ with His-Hsp17.7 (solid circles: Congo red assay, blank circles: biological activities); and (12C) 100 μM Aβ with Hsp27 (solid squares—Congo red assay, blank squares—biological activities);

FIG. 15 and FIG. 16 show representative electron micrograph images of Aβ with sHsp. The samples were mixed for 2 hours and then the pictures were taken; (FIG. 15) 100 μM Aβ and 0.1 μM His-Hsp20; (FIG. 16) 100 μM Aβ and 0.1 μM His-Hsp17.7, the length of scale bar is 100 nm;

FIG. 17 is a graph that shows the kinetics of fibril formation in the presence and absence of hsp20 Fibril formation as a function of time in the presence and absence of Hsp20 (100 μM Aβ and 100 nM Hsp20 were used; solutions were incubated with mixing at 37° C. and fibril formation was determined using Congo red binding);

FIG. 20 is a sequence alignment of M.j-sHSP and *B. bovis* HSP20: N terminal and C terminal deletions with the C-terminal deletion of HSP20=EMRRVQIDAKA (SEQ ID NO.: 5);

FIG. 21 is a graph of the size distribution of truncated Hsp20 (tHsp20);

FIG. 24 includes the amino acid sequences for the full length (SEQ ID NO:13), amino terminal truncated (SEQ ID NO:14), carboxy terminal truncated (SEQ ID NO:15), both the amino and carboxy terminal truncated (SEQ ID NO:16), a his-tagged full length (SEQ ID NO:17), a his-tagged amino terminal truncated (SEQ ID NO:18), a his-tagged carboxy terminal truncated (SEQ ID NO:19), and a his-tagged with both the amino and carboxy terminal truncated (SEQ ID NO:20) proteins that were developed for and are part of the present invention;

FIG. 25 is a gel that shows the effect of the truncations (as listed) on the target protein, and that the monomeric protein is depleted over time indicating its role in multimer formation; and FIG. 26 is a gel that shows the effect of the truncations (as listed) on the target protein, and that the monomeric protein is depleted over time indicating its role in multimer formation.

DETAILED DESCRIPTION OF THE INVENTION

Figure 1:
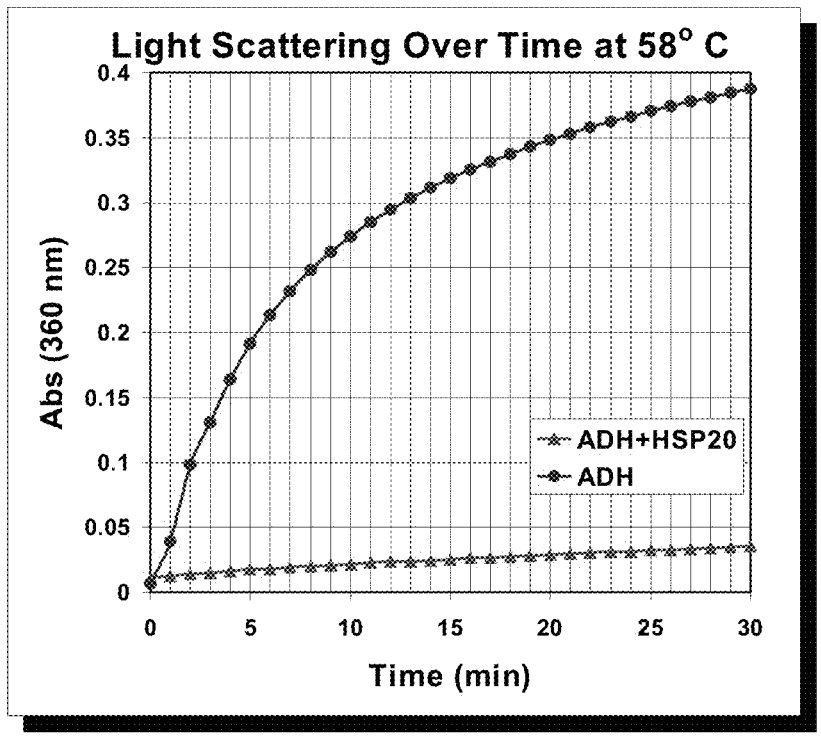
FIG. 1 is a graph of a turbidity assay used to quantitate the ability of Hsp20 to solubilize target proteins at elevated temperatures.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

β-Amyloid (Aβ) is a major protein component of senile plaques in Alzheimer's disease, and is neurotoxic when aggregated. The size of aggregated Aβ responsible for the observed neurotoxicity and the mechanism of aggregation are still under investigation; however, prevention of Aβ aggregation still holds promise as a means to reduce Aβ neurotoxicity. Alzheimer's disease (AD), the leading cause of dementia in the aging population, is accompanied by the accumulation of β-amyloid peptide (Aβ) as amyloid fibrils in senile plaques in the cerebral cortex. It is suggested by many that Aβ contributes to the neurodegeneration associated with AD via the toxicity of the peptide in aggregated form.

The superfamily of small heat shock proteins, sHSPs, are a diverse group of proteins involved in prevention of protein misfolding and the onset of programmed cell death (16, 17). They typically exist as large multimeric complexes containing 4 to 40 subunits, with molecular masses of 40 kDa or less per subunit. The sHsps bind to their substrates with high affinity and prevent protein misfolding in an ATP independent reaction (18). Generally, the α-crystallins are considered to be sHsps (15, 19). Circular Dichroism spectroscopy (CD) studies predict that β-pleated sheet dominates the secondary structure of the α-crystallins (20, 21). A conserved 90 amino acid sequence, located near the C-terminus, termed the α-crystallin domain, is the hallmark of all α-crystallins.

Other small heat shock proteins and α-crystallins have been examined for their ability to prevent Aβ and other amyloid fibril formation, with good success at relatively low molar ratios of α-crystallin to amyloid (11, 12, 22, 23). However, in none of these studies has toxicity inhibition been reported. Indeed, in work reported by others (12), αB-crystallin prevented Aβ fibril formation but enhanced toxicity. The Hsp20 protein reported herein, both reduces Aβ fibril formation at very low molar ratios, and reduces Aβ toxicity at similar molar ratios.

The present inventors have recognized and discovered that Hsp20, a novel α-crystallin isolated from the bovine erythrocyte parasite *Babesia* sp., e.g., *Babesia bovis*, is able to prevent aggregation of amyloidogenic proteins. Other members of the *Babesia* family, e.g., *Babesia bigemina*, also express Hsp20 with very high amino acid sequence conservation. It was found that the α-crystallin isolated and purified from the bovine erythrocyte parasite *Babesia bovis* prevented denaturation of alcohol dehydrogenase when the two proteins are present at near equimolar levels. The same assay may be used to initially screen other species. Next, the ability of Hsp20 to prevent Aβ amyloid formation was investigated using Congo Red binding. It was found as demonstrated herein that not only is Hsp20 able to dramatically reduce Congo Red binding, but it was also able to do so at molar ratios of Hsp20 to Aβ of 1 to 1000. Electron microscopy confirmed that Hsp20 does prevent Aβ fibril formation. Hsp20 was also able to significantly reduce Aβ toxicity to both SH-SY5Y and PC12 neuronal cells at similar molar ratios. Surprisingly, at higher concentrations of Hsp20, the protein no longer displays its aggregation inhibition and toxicity attenuation properties. The development of novel aggregation inhibitors is useful for the treatment of neurodegenerative diseases and disorders, e.g., Alzheimer's disease, that involve amyloid toxicity.

Investigation of the relationship between aggregated Aβ peptide size, structure and toxicity is ongoing. In an aggregated state containing fibrils, protofibrils, and low molecular weight intermediates/oligomers, Aβ peptide has proven to be toxic to cultured neuronal cells (1, 2). Aβ structures reported to be toxic include a non-fibrillar species of approximately 17 to 42 kDa (1), protofibrils species with hydrodynamic radii on the order of 6 to 9 nm β) and 22-35 nm or 97-367 nm (4) and fibril species, with some investigators suggesting that the smaller oligomeric Aβ species are more toxic than fibril and protofibril forms (5). Many believe that one strategy for preventing neurodegeneration associated with AD is the prevention of aggregation of Aβ into its toxic oligomeric or fibril forms.

Inhibitors of Aβ aggregation have been investigated with the aim of preventing Aβ toxicity (6-9). Some of these inhibitors are small peptides with sequences that mimic the sequence of Aβ believed to be essential for aggregation and fibril formation (8). Peptide inhibitors of this class have been able to prevent Aβ toxicity by altering the aggregated structure when added at inhibitor to Aβ molar ratios of 1:1 (8, 10). The use of molecular chaperones including α-crystallins and other small heat shock proteins has also been explored as a means of preventing Aβ aggregation and toxicity. For example, human sHsp27 inhibited Aβ1-42 fibril formation (11). When αB crystallin was examined, it was actually found to increase toxicity and 13 pleated sheet content of Aβ1-40 although it prevented fibril formation of Aβ in vitro at inhibitor to Aβ molar ratios of 1:1 or 1:5 (12).

The present invention is a novel small heat shock protein, Hsp20, isolated from the erythrocyte parasite *Babesia bovis* to prevent aggregation of Aβ and Aβ toxicity. It is shown herein that Hsp20 has α-crystallin-like properties, and that it prevents aggregation of denatured alcohol dehydrogenase. Hsp20 also prevents amyloid formation of Aβ as indicated by Congo Red binding at molar ratios of Hsp20 to Aβ of 1:1000. Hsp20 attenuated the toxicity of Aβ in SH-SY5Y and PC12 neuronal cells at analogous molar ratios. Furthermore, Hsp20 appears to be able to prevent Aβ aggregation via a novel mechanism and at much lower concentrations than what has been necessary to prevent aggregation with other inhibitors. Hsp20 may be a useful molecular model for the design of the next generation of Aβ aggregation inhibitors to be used in the treatment of AD.

Materials. Aβ(1-40) was purchased from Biosource International (Camarillo, Calif.). Cell culture reagents were purchased from GibcoBRL (Grand Island, N.Y.). All other chemicals were obtained from Sigma (St. Louis, Mo.) unless otherwise stated. His-tagged-Hsp20 was produced and isolated in E. coli. Previously, Hsp20 had been made as a fusion protein with Maltose binding protein (MBP), however, it was found that the MBP-Hsp20 did not show the effects described and claimed herein (13).

Aβ Peptide Preparation. Stock solutions of 10 mg/ml Aβ(1-40) peptides were dissolved in 0.1% (v/v) trifluoroacetic acid (TFA) in water. After incubation for 2030 min. at 25° C., the peptide stock solutions were diluted to concentrations of 0.5 mg/ml by addition of sterile phosphate buffered saline (PBS; 0.01 M $NaH_2PO_4$, 0.15 M NaCl, pH 7.4). The peptides were diluted to final concentrations of 20 μM, 50 μM, and 100 μM by addition of PBS for Congo Red and electron microscopy (EM) studies. Cell culture medium (below) replaced PBS in toxicity studies. These solutions were rotated at 60 revolutions per minute at 25° C. for 24 hours to ensure aggregation.

Cell Culture. Human neuroblastoma SH-SY5Y cells (obtained from Dr. Evelyn Tiffany-Castiglioni, College of Veterinary Medicine, Texas A&M University, College Station, Tex.) were cultured in minimum essential medium (MEM) supplemented with 10% (v/v) fetal bovine serum (FBS), 3 mM L-glutamine, 100 U/ml penicillin, 100 μg/ml streptomycin, and 2.5 μg/ml amphotericin B (fungizone) in a humidified 5% (v/v) $CO_2$/air environment at 37° C. Rat pheochromocytoma PC12 cells (ATCC, Rockville, Md.) were cultured in RPMI medium supplemented with 10% (v/v) horse serum, 5% (v/v) FBS, 3 mM L-glutamine, 100 U/ml penicillin, 100 μg/ml streptomycin, and 2.5 μg/ml fungizone in a humidified 5% (v/v) $CO_2$/air environment at 37° C. For the toxicity assays, cells were plated at a density of $1 \times 10^5$ cells/well in 96 well plates and aggregated peptide solutions were added to the cells 24 hours after plating.

Congo Red Binding. Congo Red studies were performed to assess the presence of amyloid fibrils in Aβ solution. Congo Red dye was dissolved in PBS to a final concentration of 120 μM. Congo Red solution was added to the peptide solutions at the ratio of 1:9. The peptide solution and control solution were allowed to interact with Congo Red for 30-40 minutes prior to absorbance measurement with a Model 420 UV-Vis spectrophotometer (Spectral Instruments, Tucson, Ariz.) at 25° C. The fibril formation of the samples was estimated from the absorbance using equation (1);

$$[A\beta_{Fib}] = (^{541}A_t/4780) - (^{403}A_t/6830) - (^{403}A_{CR}/8620) \quad (1)$$

where $[A\beta_{Fib}]$ is the concentration of Aβ fibril, $^{541}A_t$, $^{403}A_t$ and $^{403}A_{CR}$ are the absorbances of the sample and Congo Red at the wavelength of 541 nm and 403 nm, respectively (14). From these data, relative fibril concentrations were calculated as the ratio of sample fibril concentration to pure Aβ fibril concentration.

MTT Reduction Assay. Cell viability was measured 24 hours after peptide addition to cells using the 3, (4,5-dimethylthiazol-2-yl) 2,5-diphenyl-tetrazolium bromide (MTT) reduction assay. 10 μl of 12 mM MTT was added to 100 μl of cells plus medium in a 96 well plate. The cells were incubated with MTT for 4 hours in a $CO_2$ incubator. Then, 100 μl of a 5:2:3 N,N-dimethylforamide (DMF):sodium dodecyl sulfate (SDS):water solution (pH 4.7) was added to dissolve the formed formazan crystals. After 18 hours of incubation in a humidified $CO_2$ incubator, the results were recorded by using an Emax Microplate reader at 585 nm (Molecular Devices, Sunnyvale, Calif.). Percentage cell viability was calculated by comparison between the absorbance of the control cells and that of peptide or peptide:Hsp20 treated cells. Relative cell viability increase, was calculated from the ratio of the difference in cell viability of Hsp20:Aβ treated cells and cells treated with pure Aβ, divided by viability of cells treated with pure Aβ.

Electron Microscopy (EM). 200 μl of Aβ peptide solution, prepared as described above, was mixed, placed on glow discharged grids, and then negatively stained with 1% aqueous ammonium molybdate (pH 7.0). Grids were examined in a Zeiss 10 C transmission electron microscope at an accelerating voltage of 80 kV. Calibration of magnification was done with a 2,160 lines/mm crossed line grating replica (Electron Microscopy Sciences, Fort Washington, Pa.).

Turbidity Assay. ADH Turbidity Assay. Light Scattering of ADH and Hsp20 was performed as previously described (15). Briefly, the aggregation of ADH and Hsp20 in solution was measured by the apparent absorption due to scattering at 360 nm in a Gilford Response II spectrophotometer at 58° C. Solutions were mixed at room temperature in 50 mM phosphate buffer, pH 7.0 and analyzed immediately. 1.625 μM ADH was used in all studies. Hsp20 concentrations were varied to obtain different molar ratios of Hsp20 to ADH. Absorbance readings were taken at 1 minute intervals for one hour.

Aβ Turbidity Assay. Aβ samples were prepared as described for other studies, however, aggregation took place without mixing at 4° C. These conditions were chosen to slow down the rate of aggregation. Hsp20 was added to Aβ samples either at the beginning of incubation or after 6 days (a time insufficient for large changes in turbidity to be observed). Turbidity was determined by measuring sample absorbance at 400 nm on the UV-vis spectrophotometer.

Statistical analysis. For each study, at least 3 independent determinations were made. Significance of results was determined via the student t test with $p<0.05$ unless otherwise indicated. Data are plotted as the mean plus or minus the standard error of the measurement.

Characterization of Hsp20. Hsp20 is a 177 amino acid, 20.1 kDa protein isolated from Babesia sp., specifically Babesia bovis, a protozoan bovine erythrocyte parasite (13). Initial characterization by BLAST search of the NCBI database indicated sequence similarity with the α-crystallin family of small heat shock proteins. Hsp20 contains a region near its C-terminus that corresponds to the ~95 amino acid α-crystallin domain common to members of this protein family. These proteins are thought to be involved in the cellular response to stress. Previous work (Ficht, unpublished observation) has revealed that Hsp20 expression is up-regulated in times of thermal, nutritional and oxidative stress to the organism. Based on the apparent involvement of Hsp20 in the stress response coupled with its homology to the α-crystallins, α-crystallin activity assays were applied to Hsp20.

For the His-Tag Hsp20 expression construct, the following primers were used: Primer: F32901FT forward primer for hsp20 with Tobacco Etch Virus (TEV) protease site immediately upstream:

```
                                          (SEQ ID NO.: 3)
5'-GAA AAT CTT TAT TTT CAA GGT ATG TCG TGT

ATT ATG AGG TGC-3';
```

The first seven (7) codons encode the TEV protease site, the last seven (7) codons are the beginning of the hsp20 coding sequence:

Primer: F32901RT Reverse nrimer for hsp20 with in-frame stop:

(SEQ ID NO.: 4)
5'-CTA TTA GGC CTT GGC GTC AAT CTG AAC-3';

There primers were used to PCR a 621 coding region.

Ligation/Transformation of above insert. The Invitrogen protocol pTrcHis and pTrcHis2 TOPO TA Expression Kits Version I were used to ligate and transform the PCR product, relevant portions and solutions incorporated herein by reference. The PCR reactions were incubated directly with the TOPO plasmid according to the manufacture's protocol. This resulted in ligation of the PCR product into the pTrcHis vector. Transformed vector into chemically competent TOP10 cells (Invitrogen) and screened on LB/amp50 plates.

Directional PCR of transformants to screen for possible clones. The ProBond Purification System protocol version I from Invitrogen was used. The Hybrid protocol was modified and used to purify Hsp 20 from the lysate. Cells were grown to OD600 of 0.5 and induced with 1 mM IPTG for 5 hours, spun down and the removed media. The cells were lysed in PBS using a French pressure cell, the lysate centrifuged and the supernatant removed. The pellet containing hsp20 was suspended in Denaturing Binding Buffer (in accordance with manufacturer's instructions, relevant portions and solutions incorporated herein by reference) containing 8M urea.

Hybrid purification procedure. Briefly, resin was washed with buffer containing 8M urea. Incubated resin with lysate pellet in 8M urea for one hour. The resin was washed with denaturing buffer and then washed with native wash buffer (no urea). Next, the protein was eluted from the resin using 100 mM EDTA in water. Dialyzed over night into PBS pH 7.0. At this point, the protein can be stored at either 4 or 25 deg. C. Frozen samples are first diluted with glycerol (20% final).

FIG. 1 is a graph of a turbidity assay used to quantitate the ability of Hsp20 to solubilize target proteins at elevated temperatures. Turbidity was measured using Light scattering of ADH, as determined by absorbance at 360 nm, at elevated temperature in the presence and absence of Hsp20. ADH at a concentration of 1.625 µM is incubated in phosphate buffer alone (open circles) and in the presence of 5.75 µM Hsp20 (closed triangles) at 58° C. for one hour.

A solution of alcohol dehydrogenase when incubated at 58° C. for 60 minutes exhibits a dramatic increase in light scattering due to denaturation of the enzyme. When Hsp20 was included in the solution at time zero in a molar ration of 2:1 Hsp20:ADH, a 2.3 fold reduction in light scattering is observed at 60 minutes. To determine the most effective molar ratio for the reduction of light scattering, a series of studies applying different molar ratios was conducted.

Figure 2:
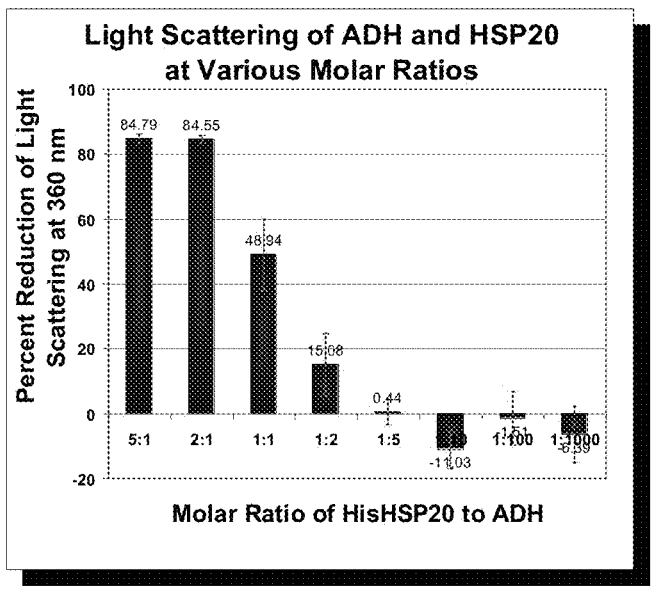
FIG. 2 is a graph that shows percent reduction of light scattering of various solutions of ADH and Hsp20 relative to ADH alone.

FIG. 2 is a graph that shows percent reduction of light scattering at time infinity of various solutions of ADH and Hsp20 relative to ADH alone. The greatest reduction in light scattering was observed at 2:1 molar ratio (Hsp20:ADH). All studies were performed at 58° C. ADH was included at 1.625 µM in each study. Light scattering at time infinity was estimated from absorbance versus time curves for each mixture. At time infinity (as determined by curve fitting software), the greatest reduction in light scattering is seen at a molar ratio of 2:1 (Hsp20 to ADH). Having established the α-crystallin activity of Hsp20 based standard assays, the ability of Hsp20 to affect Aβ(1-40) fibril formation was determined.

Effect of Hsp20 on Aβ Fibril Formation Prevention. Given that Hsp20 was able to prevent aggregation of denatured ADH, its ability to prevent aggregation and amyloid fibril formation of Aβ(1-40) was determined. Congo Red binding was used as an indicator of amyloid formation. In these studies µ50 µM µconcentrations of Aβ(1-40) were used to create fibrils. Hsp20 at concentrations from 50 µM to 2.5 µM were added to Aβ(1-40) solutions prior to aggregation. This corresponds to molar ratios of Hsp20 to Aβ of 1:1,000,000 to 1:20. After 24 hours of incubation, sufficient time for typical fibril formation, Congo Red was added to samples to assess fibril formation.

Figure 3:
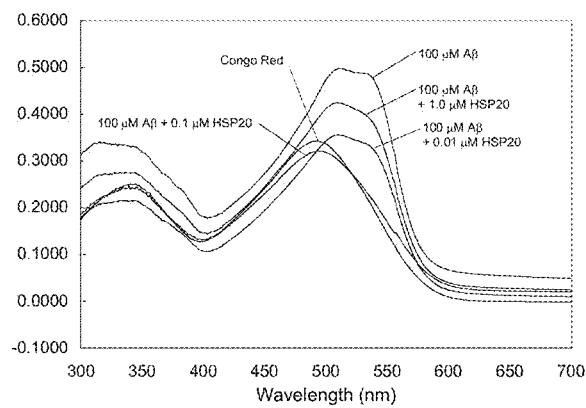
FIG. 3 is a graph of representative Congo Red absorbance spectra.

FIG. 3 is a representative absorbance spectra of Congo Red with Aβ and Aβ-Hsp20 mixtures. 100 µM Aβ(1-40) was used in all cases. Hsp20 was added at the beginning of the 24 hour aggregation at room temperature with mixing. Hsp20 alone did not alter Congo Red absorbance. Pure Aβ(1-40) solutions caused a characteristic shift in absorbance to longer wavelengths and an increase in intensity. Hsp20, when added to Aβ prior to aggregation, attenuated the shift in absorption and increase in intensity associated with Aβ fibril formation.

Figure 4:
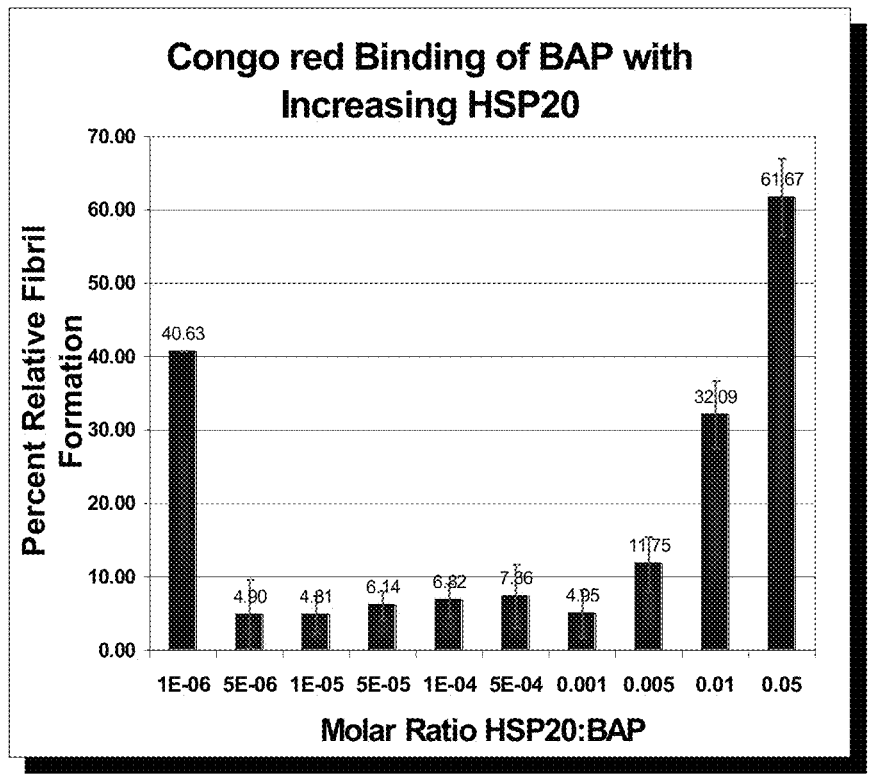
FIG. 4 is a graph that shows the effect of Hsp20 on reduction of Aβ fibril formation at different concentrations of Aβ and Hsp20.

FIG. 4 is a graph that summarizes the effects of Hsp20 on reduction of Aβ fibril formation at different concentrations of Aβ and Hsp20. At Hsp20 concentrations below 0.41M, Aβ fibril formation decreased as a function of Hsp20 concentration. However, Hsp20 became less effective at preventing Aβ fibril formation in the higher concentration range. The concentration of Hsp20 needed for optimal prevention of fibril formation appeared to be a function of Aβ concentration, with the lowest concentration of Aβ exhibiting the optimum in prevention of fibril formation at the lowest Hsp20 concentration. Fibril formation is reported relative to fibril formation seen with pure Aβ solutions. Mean plus or minus standard deviation of at least 3 independent studies are show (open circles—20 µM Aβ: squares—50 µM Aβ: triangles—100 µM Aβ).

The optimum in fibril formation for the concentration of Aβ tested occurred at the molar ratios between 0.000005 and 0.001 of Hsp20 to Aβ. The molar ratio of Hsp20 to Aβ needed to optimally prevent fibril formation is several orders of magnitude lower than that needed to prevent aggregation of ADH.

FIGS. 5A to 5C are electron micrographs of Aβ fibrils, Hsp20, and Aβ-Hsp20 mixtures that correspond to conditions used in the Congo Red binding studies. These representative electron micrographs of Aβ and Hsp20 were taken after 24 hours of aggregation (5A) 100 µM Aβ, (5B) 0.1 µM Hsp20, and (5C) 100 µM Aβ+0.1 µM Hsp20. In the images, 100 µM Aβ and 0.1 µM Hsp20 were used. As seen in FIG. 5A, Aβ formed long individual fibrils and groups of long fibrils under the aggregation conditions employed. Hsp20, at 0.1 µM and room temperature, formed species of approximately 13.6 nm in diameter, composed of 2 subunits, 5.4 nm in width each, with a distance of 2.7 nm between subunits (FIG. 5B). In micrographs of the Aβ-Hsp20 mixture (FIG. 5C), small globular species with a 16.3 nm diameter and variable length were observed. These species could be an Hsp20-Aβ complex, large Hsp20 aggregates, and/or Aβ-protofibrils. Aβ fibrils were noticeably absent from micrographs of Aβ-Hsp20 mixtures.

Ability of Hsp20 To Prevent Toxicity of Aβ. Aβ is typically toxic to neuron-like cells (SY5Y cells, and PC12 cells etc.) when in aggregated form. The effect of Hsp20 on Aβ toxicity was measured using the MTT assay for 100 µM Aβ added to SH-SY5Y cells and 2 µM Aβ added to PC12 cells.

FIG. 6 is a graph that plots cell viability as a function of Hsp20 concentration. In FIG. 6, the relative cell viability of SY5Y cells (triangles) and PC12 cells (circles) treated with 100 µM (triangles) and 2 µM (circles) Aβ as a function of Hsp20 concentration is shown. Viability was measured via the MTT reduction assay. N is greater than or equal to 6. Aβ(1-40) was incubated for 24 hrs. in the media prior to addition to the cells. Viability as a function of molar ratio of Hsp20 to Aβ; viability is reported relative to Aβ treated cells. Hsp20 by itself had no effect on SH-SY5Y or PC12 cell viability. However, Hsp20, when added to Aβ prior to aggregation, had a profound effect on Aβ toxicity observed in both cell types. It appears that the two viability curves as a function of Hsp20 to Aβ molar ratio are superimposed. The molar ratio of Hsp20 to Aβ needed for optimal toxicity attenuation is approximately the same as the molar ratio needed for optimal fibril formation prevention.

Ability of Hsp20 to reverse Aβ aggregation. In studies parallel to those described above, the ability of Hsp20 to reverse fibril formation, once Aβ was aggregated, was determined. Under conditions analogous to those described previously, and after 24 hours of Aβ aggregation, Hsp20 was added at optimal concentrations to prevent fibril formation (100 nM), incubated for up to 2 days, and then assessed fibril content via Congo Red binding. At all time points measured, fibril formation after addition of Hsp20 was equal to or greater than fibril formation of Aβ alone after 24 hours aggregation (data not shown). In all cases, viability of SH-SY5Y cells, as measured by the MTT assay, treated with solutions in which Hsp20 was added after 24 hour Aβ aggregation was not significantly greater than viability of cells treated with Aβ that had been allowed to aggregate for 24 hours (data not shown).

Ability of Hsp20 to prevent later steps in Aβ aggregation. In order to assess if Hsp20 could prevent Aβ aggregation, even if added after the beginning of aggregation, a second set of aggregation conditions was developed in which initial aggregation events (such as fibril nucleation) may occur more slowly. 100 µM Aβ were allowed to aggregate at 4° C. without mixing and measured aggregation via changes in turbidity of the Aβ solution.

Figure 7:
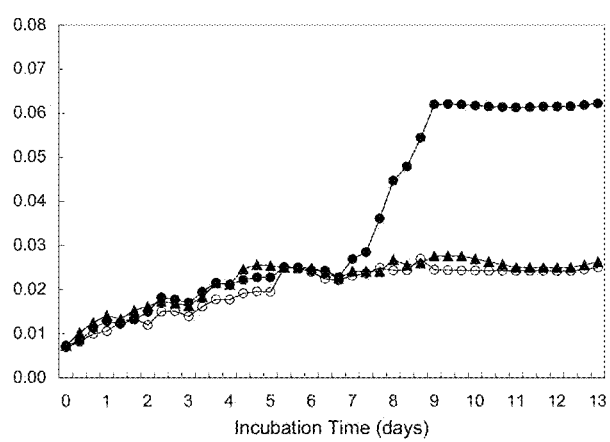
FIG. 7 is a graph of turbidity of protein aggregates as a function of time.

FIG. 7 is a graph of turbidity of protein aggregates as a function of time. Aβ was allowed to aggregate under these conditions, a rapid rise in turbidity was observed after 6 days incubation. Samples are incubated at 4° C. without rotation (closed circles—100 µM Aβ(no Hsp20): open circles). Hsp20 was added to 100 µM Aβ at the beginning of Aβ incubation: triangles—Hsp20 addition to 100 µM Aβ at 6 day after Aβ incubation.

When Hsp20 was added (final concentration of 100 nM) at the beginning of aggregation, no dramatic increase in turbidity was observed. These results are consistent with Congo Red and electron microscopy results obtained under rapid aggregation conditions. Similarly, when Hsp20 (final concentration of 100 nM) was added to the Aβ solutions at day 6, again no dramatic increase in turbidity was observed.

Electron micrographs of samples prepared under slow Aβ aggregation conditions clearly indicated the presence of fibrils both in the presence and absence of Hsp20, however, possibly less lateral fibril aggregation was observed in solutions containing Hsp20 (micrographs not shown).

Toxicity of Aβ solutions prepared via slow aggregation (at 4° C. without mixing) with and without Hsp20, was measured. In all cases, toxicity was largely unchanged upon addition of Hsp20, regardless of when Hsp20 was added in the aggregation process (data not shown).

The Hsp20 isolated, purified and characterized herein from the bovine erythrocyte parasite *Babesia bovis* (13) was demonstrated to have α-crystallin activity in vitro. The apparent light scattering of alcohol dehydrogenase in solution at 58° C. is reduced when in the presence of equimolar concentrations of recombinant Hsp20 (FIG. 1). This indicates reduced aggregation of denatured ADH at the elevated temperature due to an interaction with Hsp20. The optimal Hsp20 to ADH binding ratio is 2:1 (FIG. 2), consistent with the stoichiometry of binding one Hsp20 dimer to one ADH molecule. This is consistent with the observations of van Montfort et al (20) that other alpha crystallins are active as dimers. In addition, Hsp20 is upregulated under heat shock conditions (42° C.) and oxidative stress (molecular $O_2$ and $H_2O_2$); and, as other α-crystallins, it also forms higher order complexes as revealed through dynamic light scattering analysis (unpublished observation). Hsp20 has limited nucleotide and amino acid sequence homology to members of the α-crystallin family, with the majority of the identical/conserved amino acids occurring in the region corresponding to the α-crystallin domain (13). The α-crystallin-like activity and ability to prevent protein aggregation of Hsp20 indicate that it may be potentially useful as an aggregation inhibitor (or a model for an aggregation inhibitor) for Aβ. In view of its divergent sequence, this α-crystallin may have entirely unique properties.

As show herein in FIGS. 3-5A-5C, that Hsp20 prevents Aβ fibril formation as indicated by the absence of Congo Red binding and of visible fibrils in electron micrographs, at molar ratios near 1:1000 Hsp20 to Aβ. This is in sharp contrast to the near 1:1(2:1, or even 4:1 if ADH is considered a dimer) molar ratio needed to prevent ADH aggregation. A number of investigators have explored the ability of other small heat shock proteins, molecular chaperones, and α-crystallins to prevent fibril formation in several systems including Aβ (11, 12, 22, 23). Most have found that the chaperones or small heat shock proteins can inhibit Aβ aggregation at molar ratios of chaperone to Aβ of 1:10 to 1:100. The low concentrations of Hsp20 and other α-crystallins needed to prevent fibril formation, relative to that needed to prevent ADH aggregation, could be related to specificity of the α-crystallins for β-sheet or fibril forming proteins. Alternatively, the difference in molar ratios needed to prevent ADH aggregation relative to those needed to prevent Aβ fibril formation may be related to the temperature differences at which the studies were carried out. The ADH aggregation studies were carried out at elevated temperature, while the Aβ fibril formation studies were carried out at room temperature. The quaternary structure of α-crystallins are generally temperature dependent; however, most often, more highly active oligomers (dimers) are formed at higher temperatures (20, 24).

Hsp20 may interact with an oligomer of Aβ in a near 1 to 1 molar ratio; however, the Aβ oligomer may be very dilute in Aβ solutions. In models of Aβ aggregation, investigators postulate that Aβ forms micelles or multimeric nuclei from Aβ monomers or dimers via a high order process (25-27). It is from these micelles or nuclei that fibril growth is initiated. Micelles or nuclei would be far less abundant than monomeric Aβ. Hsp20 binding may lead to removal of fibril initiating species from solution, thereby preventing Aβ fibril formation.

As seen in FIG. 4, there is an optimum concentration of Hsp20 for Aβ fibril formation prevention. Oligomerization dynamics of α-crystallins are concentration dependent (28). Hsp20 may aggregate to form a less active structure at higher concentrations. High molecular weight oligomers of heat shock proteins, which tend to form at high concentrations, are less active than the low molecular weight oligomers (29). Additionally, equilibrium distribution of oligomeric Hsp20 species are likely to dependent upon conformers or oligomers of substrate Aβ present in solution.

Analogous to fibril formation prevention data, Hsp20 attenuates Aβ toxicity at similar molar ratios (FIG. 6). These data suggest that the Aβ species which bind Congo Red and have fibril appearance on electron micrographs are toxic. Non-fibrillar ADDLs, low molecular weight oligomers, protofibrils, and fibrils have all been found to be toxic (1, 3). In some cases oligomeric Aβ has been found to be more toxic than fibril Aβ (5). These results suggest that addition of Hsp20 leads to a reduction in the formation of some of these species.

A careful examination of electron micrographs of Aβ-Hsp20 mixtures under optimal fibril formation and toxicity prevention conditions (FIG. 5A-5C) reveals the presence of small globular species with a 16.3 nm diameter and variable length. Size analysis of these globular structures suggests that the species may be an Hsp20-Aβ complex rather than Aβ protofibrils since the width of these species (16.3 nm) is atypical for Aβ micelles (5~11 nm), protofibrils (4~8 nm), or fibrils (6~10 nm) (27).

When Aβ was aggregated slowly at 4° C., Hsp20 was able to prevent large increases in turbidity when added to Aβ at a 1:1000 molar ratio of Hsp20 to Aβ (FIG. 7). Electron micrographs of species formed indicate that under these conditions Hsp20 prevented some lateral aggregation of fibrils but did not prevent fibril formation. In addition, with slow aggregation, Hsp20 did not prevent toxicity. Thus, lateral aggregation of fibrils or its prevention does not appear to be associated with toxicity. These results are consistent with reports by others that Aβ oligomers are more toxic that Aβ fibrils, and that a variety of sub-fibril sized species are toxic (1-5). The inability of Hsp20 to prevent Aβ fibril formation under the conditions used may be due to temperature affects on Hsp20 oligomerization. At 4° C., there may be insufficient active Hsp20 dimers present to prevent fibril formation or hsp20 may be subject to cold denaturation and inactivation at 4° C. (data not shown). Alternatively, the energetics of the Hsp20-Aβ interaction may be adversely affected by the drop in temperature. In addition, under slow aggregation conditions, the relative abundance of the Aβ species that bind to Hsp20 may be significantly different than under rapid aggregation conditions under which the Hsp20 optimum concentration was determined.

A number of different approaches have been explored for prevention of Aβ amyloid fibril formation and toxicity. Pentapeptides such as SEQ ID NO.: 6 KLVFF (8), SEQ ID NO.: 7 LPFFD (30), SEQ ID NO.: 8 GVVIN, SEQ ID NO.: 9 RVVIA (31) have been used to disrupt Aβ fibril formation and neurotoxicity. These pentapeptides have the same or similar residues as segments of Aβ essential for fibril formation, bind to Aβ, and alter the structure that Aβ adopts (30). Generally, 1 to 1 molar ratios of peptide inhibitors to Aβ are needed in order to effectively prevent fibril formation (8). Amphipathic molecules such as hexadecyl-N-methylpiperidinium (HMP) bromide or sulfonated molecules such as Congo Red have also been used to prevent Aβ fibril formation and toxicity.

FIG. 8 is a nucleic acid sequence of an Hsp20 for use with the present invention (SEQ ID NO.: 1).

FIG. 9 is the amino acid sequence of an Hsp20 (SEQ ID NO.: 2) for use with the present invention in accordance with SEQ ID NO.: 1.

Figure 10:
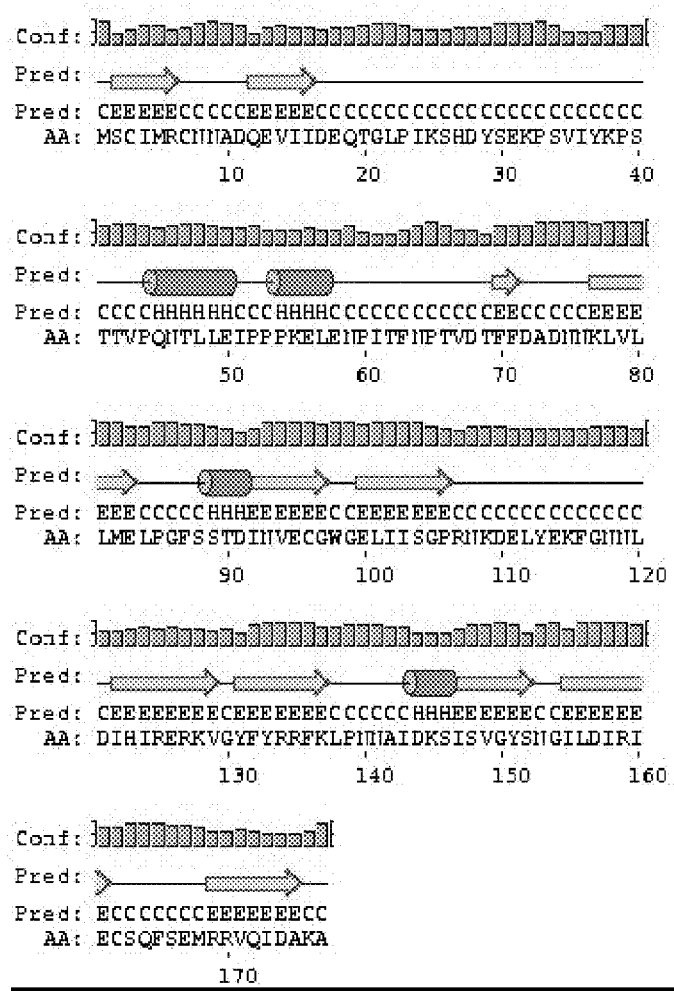
FIG. 10 is a secondary structure prediction of Hsp20.

FIG. 10 is a predicted secondary structure for Hsp20, which predicts that Hsp20 is likely to contain a large amount of beta sheet secondary structure. CD measurements were carried out to determine if these structures are present in the Hsp20 studies herein. Based on the predicted structure, subfragments of hsp20 may be produced to determine if they may have the same activity as the whole protein. For example, it has been determined that the Hsp20 active form is likely to be a dimer. As such, deletion scan may be conducted in which a small number of residues, e.g., beginning with the N-terminal 5-10 amino acid, to determine if the Hsp20 is able to form dimers. Dimers may be detected using, e.g., physical observation (antibody capture assays, magnetic bead binding, electron microscopy using gold beads of different sizes) or read out assays, e.g., fluorescence resonance electron transfer (FRET), surface plasmon resonance effects, yeast two hybrid, etc. In fact, some inactive or partially active forms of the monomer and/or dimer are also useful as controls and the like. For example, if the larger inactive complexes are not allowed to form, the hsp20 will be active over a much wider concentration range. Studies conducted to date (data not shown), for example, indicate that the intermediate forms of amyloid are the likely target for binding of hsp20. It appears to be a 10-mer in the first set of studies.

Circular Dichroism Measurements. FIG. 11 is a graph of CD measurements carried out on an AVIV model 62. The wavelength scan was performed at various temperatures from 250 to 200 nm reading every 0.5 nm and averaging each reading for 5 seconds. Circular Dichroism revealed a high beta sheet secondary structure, typical of α-crystallin domains. In vivo studies have revealed properties unique to this α-crystallin.

As described hereinabove, the heat shock protein, Hsp20 from *B. bovis* prevents Aβ aggregation and toxicity at very low concentrations of small heat shock protein relative to Aβ(1:1000). A series of studies were conducted to examine the mechanism of Hsp20 activity and compare it to activity of other small heat shock proteins. The aggregation and toxicity prevention properties of two other small heat shock proteins, Hsp17.7 from carrot, and human recombinant Hsp27 were examined. Both sHsps inhibited Aβ1-40 aggregation but not toxicity. Electron microscope images of Hsp-Aβ complexes that formed under conditions and where both aggregation and toxicity prevention were observed were compared to Hsp-Aβ complexes that formed when only aggregation prevention was seen (data not shown). In cases where both aggregation and toxicity prevention were seen, a large ring structure was observed repeatedly, which was absent when aggregation was prevented, but toxicity was not prevented. For discussion, but by no means a limitation to this invention, it may be postulated the Hsp20-Aβ interaction leads to both toxicity and aggregation prevention. The present invention provides constructs, vectors, proteins, methods and the like for preventing protein aggregation and toxicity of Aβ as well as detailed instructions for designing the next generation of Aβ aggregation inhibitors to be used in AD.

β-Amyloid (Aβ)-(1-40) was purchased from AnaSpec (San Jose, Calif.) and Biosource International (Camarillo, Calif.). Recombinant human Heat Shock Protein 27 (Hsp27) was purchased from MBL International Corporation (Woburn, Mass.). Human neuroblastoma SH-SY5Y cells (ATCC number: CRL-2266) were purchased from ATCC (Manassas, Va.). Cell culture reagents were purchased from Invitrogen Life Technologies (Carlsbad, Calif.). Congo red was purchased from Fisher Chemicals. (Pittsburgh, Pa.). All other chemicals, unless otherwise specified Ire obtained from Sigma-Aldrich Co.

Heat Shock Protein 20 (Hsp20) Preparation Hsp20. was isolated from *Babesia bovis*, [12] and Hsp20 with the N-terminal polyhistidine fusion protein was produced in recombinant *E. coli*. Hsp20 was prepared by growing cells to $OD_{600}$ of 0.5 followed by induction with 1 mM IPTG for 5 hours, and removal of media. The cells were then lysed in PBS using a French pressure cell and the insoluble His-Hsp20 pellet collected. The pellet containing His-Hsp20 was suspended in Denaturing Binding Buffer (Invitrogen) containing 8M urea and incubated with Probond resin for 1 hour to allow binding of His-Hsp20 to the nickel chromatography resin. The protein was eluted from the resin using 100 mM EDTA, dialyzed overnight into PBS pH 7.0, 20% glycerol and frozen at −80° C. Protein purity and molecular weight were confirmed by SDS PAGE.

Heat Shock Protein 17.7 (Hsp17.7) Preparation. The gene, encoding Hsp17.7 from carrot, was cloned in *E. coli* (M. K. Malik, J. P. Slovin, C. H. Hwang, and J. L. Zimmerman, Modified expression of a carrot small heat shock protein gene, hsp17.7, results in increased or decreased thermotolerancedouble dagger, Plant J. 20 (1999) 89-99). *E. coli* was grown in the LB media (Tryptone (10 g/L), Yeast Extract (5 g/L) and NaCl (10 g/L)) with 50 µg/ml kanamycin broth on the wheel for aeration overnight. The tubes of LB broth were inoculated at a 1:200 dilution and put on wheel at 37° C. 100 mM IPTG was added to cells in order to induce Hsp17.7 when *E. coli* reached an OD600 of 0.6. *E. coli* was put back on the wheel and Hsp17.7 was expressed at 37° C. overnight. The cells were harvested by centrifugation at 6,000 rpm for 10 minutes and frozen at −20° C. overnight. The cells were lysed with 20 mM imidazole and 10 min sonication. Hsp17.7 was purified by using a metal affinity column (POROS® MC) (Framingham, Mass.) with copper chromatography resin. (Self Pack™ POROS® 20MC Media) (Framingham, Mass.) The protein was eluted by pH gradient from pH 7.4 (Phosphate buffer, 50 mM NaH2PO4, and 300 mM NaCl) to pH 4.5 (Phosphate buffer). Protein purity and molecular weight were confirmed by size exclusion chromatography.

Protein Sample Preparation. Aβ1-40 was dissolved in 0.1% (v/v) Trifluoroacetic acid (TFA) solvent at the concentration of 10 mg/ml. This solution was incubated at room temperature for 20~30 minutes in order to completely dissolve the Aβ. Filtered phosphate-buffered saline (PBS, 4.3 mM Na2HPO4, 137 mM NaCl, 2.7 mM KCl and 1.4 mM KH2PO4, pH 7.4) was added to the Aβ solution to make the final concentrations used in experiments. For cell viability assays, MEM medium was used instead of PBS buffer. Aβ samples were mixed on the rotator at 18 rpm and 37° C., and samples were taken out as a function of time. sHsps were added to the Aβ samples before the samples were incubated (prior to aggregation).

Congo Red Binding. Congo red was dissolved in PBS at the concentration of 120 µM and syringe filtered. The Congo red solution was mixed with protein samples at 1:9 (v/v) ratios to make the final concentration of Congo red 12 µM. After a short vortex, the mixtures were incubated at room temperature for 3040 minutes. Absorbance measurements from 400 nm to 700 nm were taken (UV-Vis spectrometer model UV2101, Shimadzu Corp.; Kyoto, Japan). Alternatively, Congo red absorbance was read at 405 nm and 540 nm using an Emax Microplate Reader (Molecular Devices, Sunnyvale, Calif.). In both cases, PBS buffer was used as a blank. The concentration of Aβ fibrils was estimated from Congo red binding via equation (1):

$$[A\beta_{FIB}] = (^{541}A_t/4780) - (^{403}A_t/6830) - ^{403}A_{CR}/8620) \quad (1)$$

where $^{541}A_t$ and $^{403}A_t$ are the absorbances of the Congo red-Aβ mixtures at 541 nm and 403 nm, respectively, and $^{403}A_{CR}$ is the absorbance of Congo red alone in phosphate buffer. [27] In Microplate reader, absorbances at 405 nm and 540 nm were assumed to be same as those at 403 nm and 541 nm.

Aβ Turbidity Assay. Protein samples (100 µM Aβ and 100 µM Aβ+sHsps) were prepared as described in Protein Sample Preparation. At every 30 minutes until 8 hours, turbidity of protein samples was monitored at 405 nm using UV-Vis spectrometer (model UV2101, Shimadzu Corp.; Kyoto, Japan). PBS buffer solution was used as a blank.

Electron Micrograph (EM). 200 µl of Aβ peptide solution, prepared as described above, was mixed, placed on glow discharged grids, and then negatively stained with 1% aqueous ammonium molybdate (pH 7.0). Grids were examined in a Zeiss 10 C transmission electron microscope at an accelerating voltage of 80 kV. Calibration of magnification was done with a 2,160 lines/mm crossed line grating replica (Electron Microscopy Sciences, Fort Washington, Pa.).

Cell Culture. SH-SY5Y cells were grown in Minimum Essential Medium (MEM) supplemented with 10% (v/v) Fetal Bovine Serum (FBS), 25 mM Sodium bicarbonate, 100 units/ml penicillin, and 100 mg/ml streptomycin. Cells were cultured in a 5% (v/v) $CO_2$ environment at 37° C. incubator. Low passage number cells were used (<p20) in all experiments to reduce instability of cell line.

Biological Activity Assay. For biological activity tests, SH-SY5Y cells at a density of 1×10$^6$ cells/mL1 were grown in 96 well plates. Cells were fully differentiated by addition of 20 ng/mL NGF for 8 days. Aβ samples in MEM medium were added to the differentiated SH-SY5Y cells and the cells were incubated with Aβ samples at 37° C. for 2 hours. Negative controls (cells in medium with no Aβ) and positive controls (cells treated with 800 µM $H_2O_2$ in 50% (v/v) medium for 2 hours) were also prepared. At least 3 wells were prepared for each Aβ treatment, and each positive and negative control.

Cell viability was determined by using the fluorescent nucleic acid dye, propidium iodode (PI). PI is mostly used fluorescent dye for staining DNA in cells. PI can enter the dead cells and bind DNA in dead or late apoptotic cells. PI is a DNA specific dye and can not cross the membrane of viable cells. In order to stain the dead cells, Aβ treated cells were washed with PBS 1~2 times and 150 µL of enzyme free dissociation buffer from Gibco (Carlsbad, Calif.) was added to the cells in order to detach SH-SY5Y cells from the surface. The cells were incubated at 37° C. for approximately 5 minutes. 5 µL of 33 µM PI was added to the cells and cells were incubated for 15~20 minutes at room temperature in the dark. Stained cells in 96 well plates were loaded in the FACS array (BD FACSArray, BD Bioscience; San Jose, Calif.) and fluorescence histograms for cells were obtained. To set up gates for the cell viability assays, 2 sets of staining controls were prepared, unstained cells, and cells stained with PI alone. Cells not stained with PI dye were taken as live cells, and the relative cell viabilities were calculated using equation (2).

$$\text{Relative Cell Viability (\%)} = \frac{(L.C._{sample} - L.C._{H2O2})}{(L.C._{NControl} - L.C._{H2O2})} \times 100 \quad (2)$$

where $L.C._{sample}$ is live cells (%) of cells treated with Aβ and sHsps, $L.C._{NControl}$ is live cells (%) of negative control, and $L.C._{A\beta}$ is live cells (%) of cells treated with only Aβ.

Statistical Analysis. For each study, at least 3 independent determinations were made. Significance of results was determined via the student t test with p<0.05 unless otherwise indicated. Data are plotted as the mean plus or minus the standard error of the measurement.

Effect of Hsp20 on Aβ Aggregation and Toxicity. Aβ is toxic to neuron-type of cells when in aggregated form. Results to date indicated that His-Hsp20 has been very promising as an Aβ aggregation and toxicity inhibitor (S. Lee, K. Carson, A. Rice-Ficht, and T. Good, Hsp20, a novel alpha-crystallin, prevents A-beta fibril formation and toxicity, Protein Sci. 14 (2005) 593-601). Congo red binding was used as an indicator of extended β-sheet structure and changes in Aβ aggregation in this research. As shown in FIG. 12A, His- Hsp20 prevents Aβ aggregation, showing the characteristic U-shape pattern. At lower His-Hsp20 concentrations than 0.1 μM, Aβ fibril formation decreases as a function of His-Hsp20 concentration. However, His-Hsp20 becomes less effective at preventing Aβ fibril formation in the higher concentrations. In FIG. 12A, we also show the effect of His-Hsp20 on Aβ toxicity. His-Hsp20 prevents Aβ toxicity over wide range of concentrations. SH-SY5Y cells treated with the Hsp20-Aβ mixture shows higher cell viabilities (61.3%±2.6%-78.0%±3.6%) than those treated with 100 μM Aβ (45.3%±1.7%). Statistically, cell viabilities of Aβ itself are different from all cell viabilities of Hsp20-Aβ mixtures. (all p values between Aβ and Hsp20-Aβ mixture are less than 0.05).

Figure 12B:
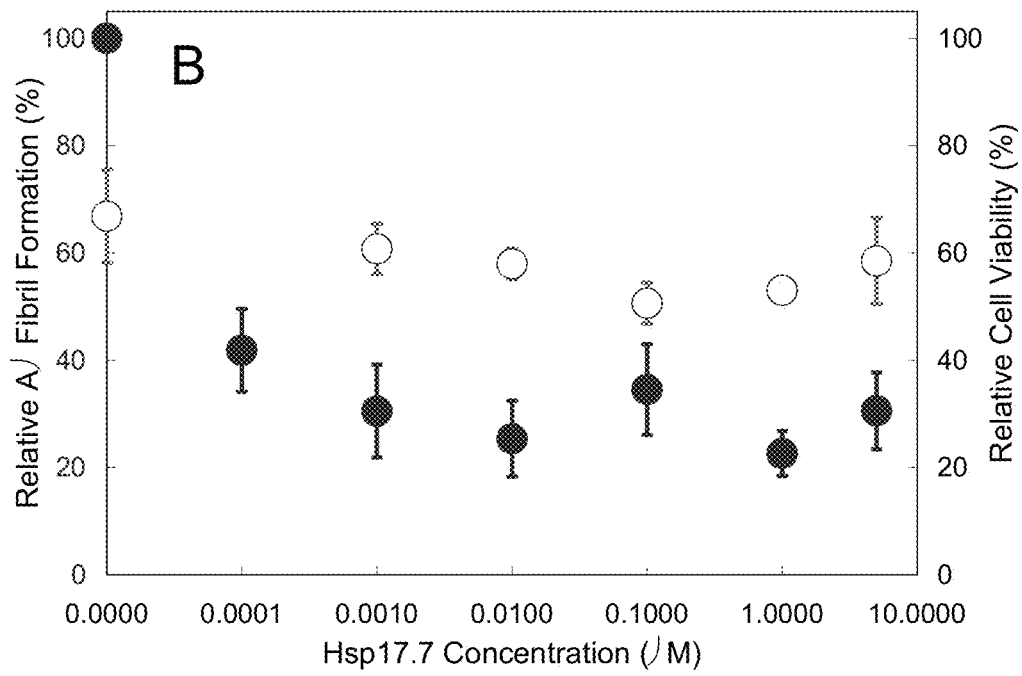

Effect of Hsp17.7 on Aβ Aggregation and Toxicity. As shown in FIG. 12B, Congo red result shows that His-Hsp17.7, a small heat shock protein derived from carrot, prevents Aβ aggregation at all concentrations between 1 nM and 20 μM, without the apparent loss of activity at even higher concentrations (up to 20 μM). As for toxicities in FIG. 12B, addition of 20 μM Aβ to SH-SY4Y cells results in about 30% toxicity. Hsp17.7-Aβ mixtures have almost same toxicities like Aβ alone. Statistically the toxicities between Hsp17.7-Ab mixture and Aβ alone are not different. (all p values are greater than 0.05 between Aβ sample and other samples containing Hsp17.7). Thus, unlike Hsp20, Hsp17.7 prevents Aβ aggregation without preventing Aβ toxicity.

Figure 12C:
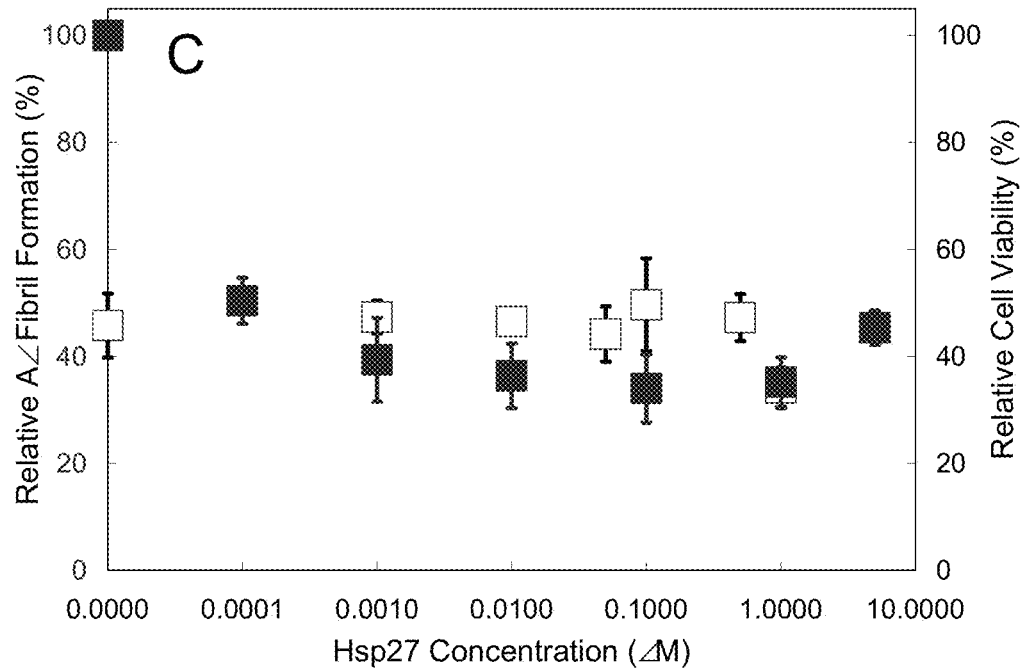

Effect of Hsp27 on Aβ Aggregation and Toxicity. FIG. 12C shows the biological activity of Aβ when incubated with Hsp27 with near the same effectiveness and at similar concentration ranges as Hsp17.7. Unlike Hsp20, Hsp27 doesn't lose its ability to prevent Aβ aggregation at high concentrations (5 μM of Hsp27). In the toxicity experiments shown in FIG. 12C, the samples containing Hsp27 incubated with Aβ have the same or more toxicity than the toxicity of Aβ alone. Statistically, cell viabilities of 100 μM Aβ with 5 nM–1 μM Hsp27 are not different from that of 100 μM Aβ. (all p values are greater than 0.05) 1 nM and 5 μM Hsp27 increases the toxicity of 100 μM Aβ. In other words, Hsp27 doesn't protect the cells from the Aβ toxicity.

Figure 13:
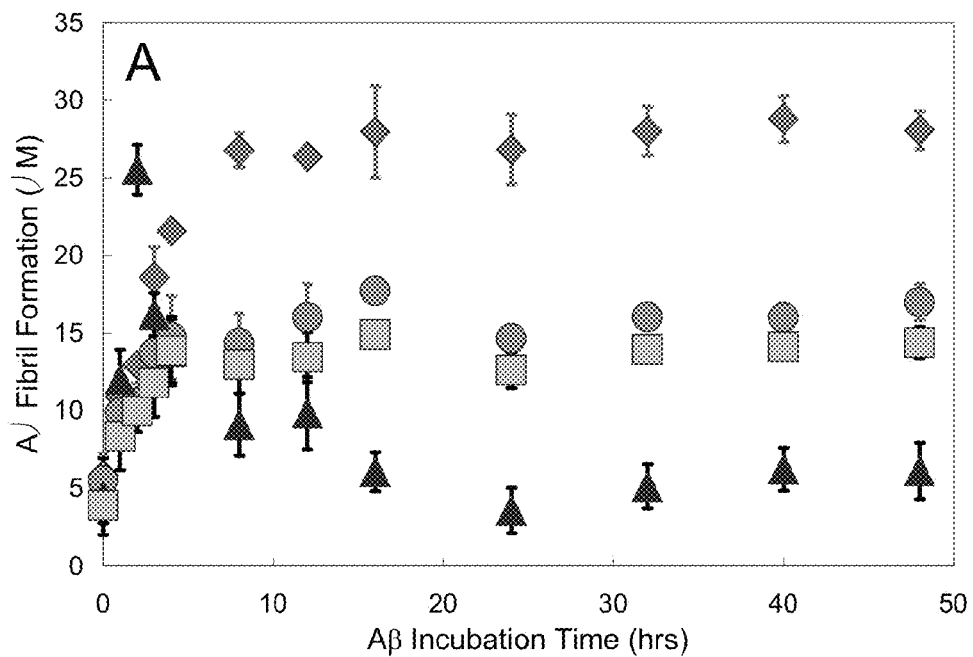
FIG. 13 and FIG. 14 show the kinetics of Aβ aggregation with sHsps. Aβ was incubated with or without sHsps and the aggregation rates were detected by FIG. 13 Congo red, and FIG. 14 Turbidity at 405 nm (dark gray diamonds—100 μM Aβ, black triangles—100 μM Aβ and 0.1 μM His-Hsp20, gray circles—100 μM Aβ and 0.1 μM His-Hsp17.7, light gray squares—100 μM Aβ and 0.1 μM Hsp27)
Figure 14:
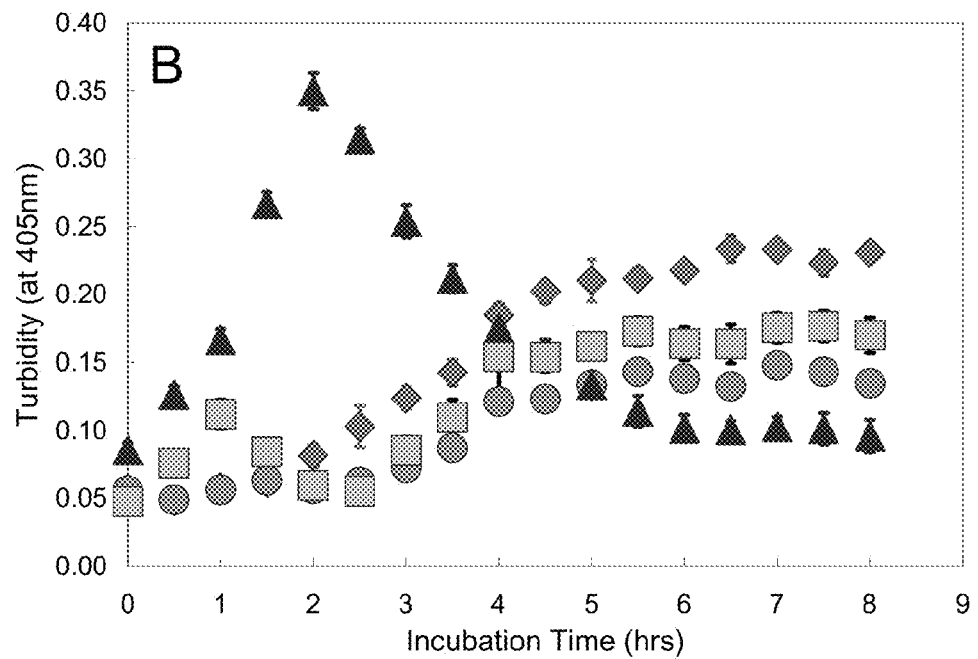

Kinetics of sHsps-Aβ Interaction (Congo red and Turbidity). For Hsp20 to be a useful aggregation inhibitor (or model for an aggregation inhibitor) for Aβ, it is important to discern if Hsp20 simply slows the rate of aggregation of Aβ, or actually alters the aggregation pathway of Aβ. To that end, kinetics of Aβ aggregation were measured as assessed via Congo red binding and turbidity in the presence and absence of sHsps. As seen in FIG. 13, Aβ aggregation increases slowly at first, followed by a period of rapid increase in fibril content, which eventually saturates over time. When Hsp20 is added at the beginning of aggregation, fibril formation and Congo red binding follow a very different pattern. Initially, aggregation is accelerated, followed by a rapid loss in fibril content and ability to bind Congo red. These results suggest that Hsp20 does not simply slow the rate of Aβ aggregation, but actually changes the fibril formation pathway, possibly sequestering a fibril initiating species that forms early during aggregation and preventing further fibril growth. Hsp 17.7 and Hsp27 also change the fibril formation pathway. However, both Hsp 17.7 and Hsp27 don't show accelerated aggregation in the early incubation time like Hsp20. Turbidity assay in FIG. 14 shows more drastic differences between Hsp20 and other sHsps. Aβ fibril formation follows a characteristic sigmoidal curve, with a lag phase at early incubation times, followed by a fibril growth phase, then a saturation phase. Aβ initially mixed with Hsp20 shows higher intensities at earlier incubation time between 0 and 4 hours, which means Hsp20-Aβ mixture forms big species. In Congo red result, Hsp20-Aβ mixture at 2 hours shows more Cong red binding than other samples. Both results suggest that Hsp20-Aβ mixture forms big size species with β-pleated sheet at earlier incubation time. Hsp27-Aβ mixture shows higher intensity at 1 hour, which doesn't make big differences after that. Hsp17.7-Aβ mixture doesn't show higher intensity at earlier incubation time.

Ability of His-Hsp20 To Prevent Toxicity of Aβ with Time. In order to assess the ability of His-Hsp20 to prevent Aβ toxicity, His-Hsp20 was added to Aβ samples prior to Aβ aggregation, and toxicity of the Hsp20-Aβ mixtures were tested as a function of time after incubation. As seen in FIG. 14, His-Hsp20 prevents Aβ toxicity. Statistically, cell viabilities of Hsp20-Aβ mixture at 2, 4, and 8 hours are not different from negative control (p=0.862, 0.087, and 0.140 for 2, 4, and 8 hours respectively, all p values are greater than 0.05), which means His-Hsp20 protects the cells from Aβ toxicity completely. At 2, 4, and 8 hours, Aβ shows only 50-70% cell viability compared to negative control. At 24 hours, Hsp20-Aβ mixtures have cell viability of about 80%, whereas Aβ shows only about 40% cell viability. Although His-Hsp20 doesn't prevent Aβ toxicity completely at 24 hours, His-Hsp20 still reduces the Aβ toxicity (viability is statistically different between Aβ and Hsp20-Aβ mixture).

Electron Micrograph (EM) Images of Aβ with Small Heat Shock Proteins. To further exam the relationship between Aβ structure, sHsp-Aβ interactions, and aggregation and toxicity prevention activities, electron microscopy was used to examine structures formed by Aβ in the presence of the small heat shock proteins. In one set of studies, structures formed by 100 μM Aβ and 0.1 μM His-Hsp20 were examined as a function of time during incubation with mixing, analogous to the kinetic data shown in FIG. 13. As early as 1-hour after incubation, Aβ and Hsp20 begin to complex ring-like structures. (data not shown).

As seen in FIG. 15, a better defined multi-ring structure is observed at two hours. The appearance of this large multi-ring structure corresponds to the maximum in Congo red binding seen in Hsp20-Aβ mixtures seen in FIG. 13. At later times, the ring structures seem to fall apart, with few rings observed in micrographs at 24 hours after incubation. (data not shown). The large multi-ring structure is only seen in micrographs of Aβ and Hsp20 when 100 μM Aβ and 0.1 μM Hsp20 are used. When the same concentration of Aβ, but higher and lower concentrations of Hsp20 are used (1 nM, 0.01 μM, 1 μM, and 5 μM Hsp20), the complex ring structure is not observed (data not shown). As seen in FIG. 16, similar electron microscopy studies were performed with Aβ and Hsp17.7. At no time during incubation of Aβ and Hsp17.7 are the large multi-ring complexes observed in micrographs. Also examined were structures formed 24 hours after incubation of Aβ and Hsp17.7, as these structures would represent the complexes added to cells in culture for toxicity assays. Some isolated fibrils from Hsp17.7-Aβ mixture are observed at 24 hours (data not shown), which is very different from Hsp20-Aβ mixture at 24 hours. Differences in these structures might point to clues as to the differences in structures formed and their relationship to cell toxicity.

In Alzheimer's disease (AD) and in dementia associated with Parkinson's disease, an increased expression of Hsp27 and of αβB-crystallin was found (T. Iwaki, A. Kume-Iwaki, R. K. Liem, and J. E. Goldman, Alpha B-crystallin is expressed in non-lenticular tissues and accumulates in Alexander's disease brain, Cell 57 (1989) 71-78; K. Renkawek, G. J. Stege, and G. J. Bosman, Dementia, gliosis and expression of the small heat shock proteins hsp27 and alpha B-crystallin in Parkinson's disease, Neuroreport 10 (1999) 2273-2276). These results suggest that chaperone activity of heat shock proteins may contribute to the pathogenesis associated with protein aggregation in Alzheimer's disease (Y. C. Kudva, H. J. Hidding a, P. C. Butler, C. S. Mueske, and N. L. Eberhardt, Small heat shock proteins inhibit in vitro A beta (1-42) amyloidogenesis, FEBS Lett. 416 (1997) 117-121).

Small heat shock proteins (sHsps) are expressed in almost all organisms when cells become stressed during exposure to unfavorable environments. Small heat shock proteins exist as large oligomeric complexes of 300-800 kDa with monomeric molecular mass of 15-43 kDa (J. I. Clark, and P. J. Muchowski, Small heat-shock proteins and their potential role in human disease, Curr. Opin. Struct. Biol. 10 (2000) 52-59; T. H. MacRae, Structure and function of small heat shock/alpha-crystallin proteins: established concepts and emerging ideas, Cell Mol. Life. Sci. 57 (2000) 899-913; I. P. van den, D. G. Norman, and R. A. Quinlan, Molecular chaperones: small heat shock proteins in the limelight, Curr. Biol. 9 (1999) R103-105.). The primary roles of sHsps are to stabilize other proteins under stress conditions and protect them from aggregation (J. M. Bruey, C. Ducasse, P. Bonniaud, L. Ravagnan, S. A. Susin, C. Diaz-Latoud, S. Gurbuxani, A. P. Arrigo, G. Kroemer, E. Solary, and C. Gamido, Hsp27 negatively regulates cell death by interacting with cytochrome c, Nat. Cell. Biol. 2 (2000) 645-652). sHsps are composed of three parts in the primary sequence, the N-terminal domain, the α-crystallin domain, and the C-terminal extension. The α-crystallin domains, highly conserved 80-100 amino acid sequences located in the C-terminal regions, are very important for substrate binding. [34] Other research groups showed that αB-crystallin prevented Aβ fibril formation in vitro, but not the toxicity (G. J. Stege, K. Renkawek, P. S. Overkamp, P. Verschuure, A. F. van Rijk, A. Reijnen-Aalbers, W. C. Boelens, G. J. Bosman, and W. W. de Jong, The molecular chaperone alphaB-crystallin enhances amyloid beta neurotoxicity, Biochem. Biophys. Res. Commun. 262 (1999) 152-156). Human Hsp27 inhibited fibril formation of Aβ1-42 in vitro, but it was less effective on the pre-formed amyloid.

In FIG. 12A, Hsp20 prevented Aβ aggregation over 80% in the Hsp20 concentration of 1 nM-1 μM, and also reduced Aβ toxicity in this ranges. FIGS. 12B and 12C show that both Hsp 17.7 and Hsp27 prevent Aβ aggregation but not toxicity. Therefore, it was found that Hsp17.7 and Hsp27 prevents only Aβ1-40 aggregation, whereas Hsp20 prevents Aβ1-40 aggregation and toxicity. The α-crystallin domains of these sHsps could be the crucial parts of the proteins in preventing Aβ aggregation because the α-crystallin domains are well-conserved regions and are found in Hsp20, Hsp17.7, and Hsp27. The results of sequence homologies using the software CLUSTALW (EMBL-European Bioinfomatics Institude) show that the sHsps lack sequence homology in both the N-terminus, and C-terminal extension. (32%—αB-crystallin and Hsp27, 15%—αB-crystallin and Hsp17.7, 8%—αB-crystallin and Hsp20, 17%—Hsp20 and Hsp17.7, 7%—Hsp20 and Hsp27, and 7%—Hsp17.7 and Hsp27). These differences could result in different binding affinity between sHsp and Aβ or in different mechanisms by which when they prevent Aβ aggregation. In FIG. 13 and FIG. 14, sHsps-Aβ mixtures don't change the Congo red and turbidity with time in the saturation phase, which are parallel to Aβ. It suggests that all sHsps prevent Aβ aggregation by changing Aβ aggregation pathways rather than slowing down Aβ aggregation. In FIG. 13 and FIG. 14, Hsp20 shows very different pattern to prevent Aβ aggregation from other sHsps. One of the possible explanations is that Hsp20 has stronger binding affinity with Aβ than other sHsps. Different binding affinity results in Hsp20 binding to Aβ in earlier stage of Aβ aggregation which are not toxic species to the cells, whereas other sHsp bind to Aβ in later stage of Aβ aggregation. As a result, Hsp20 prevents Aβ aggregation more than other sHsp in FIG. 12A, 12B and FIG. 12C.

Apparently, the large multi-ring formation of Hsp20 with Aβ seems to be related to the ability of Hsp20 to prevent both Aβ aggregation and toxicity. FIGS. 13, 14 and 15 indicate that only Hsp20 forms a large multi-ring structure with Aβ (at 2 hours in mixing condition), whereas the other sHsps were not observed to form ring structures. The stoichiometric binding between Hsp20 and Aβ could be associated with the large multi-ring formation and optimum activity of Hsp20 in prevention of Aβ aggregation. In order to know the effect of Hsp20 assembly on Aβ aggregation, a novel Hsp20 construct was prepared that was missing 11 residues from the C-terminus that are partly responsible for Hsp20 assembly. This form of Hsp20 forms stable dimers under most conditions. The activities of the non-aggregating form of Hsp20 and the aggregating Hsp20 were compared, and find little difference in their aggregation prevention and toxicity behaviors (data not shown). These results suggest that the binding ratio (stoichiometric binding) between Hsp20 (dimer) and Aβ is more important in Aβ aggregation prevention than Hsp20 assembly. Other sHsps could follow different mechanism via assembly from Hsp20. First, sHsps could assemble to form oligomeric complexes such as hollow cylindrical or spherical structure, and then sHsp assemblies protect the hydrophobic parts of Aβ from aggregation.

These results demonstrate that Hsp20 may have a unique mechanism of interaction with Aβ that results in different activity in Aβ toxicity prevention relative to other sHsps. FIG. 14 shows that Hsp20-Aβ mixture has the same cell viabilities as negative control until 8 hours, although Hsp20 doesn't protect the cells completely from Aβ toxicity at 24 hours. Again, Hsp20 can delay Aβ toxicity via a unique mechanism of interaction with Aβ. In Alzheimer's disease, even delaying Aβ aggregation onset or slowing its progression might be therapeutically useful, as disease onset is late in life.

The kinetics of amyloid formation changes in the presence of hsp20. It is not simply a slowing of the process but the use of a different pathway.

Figure 18:
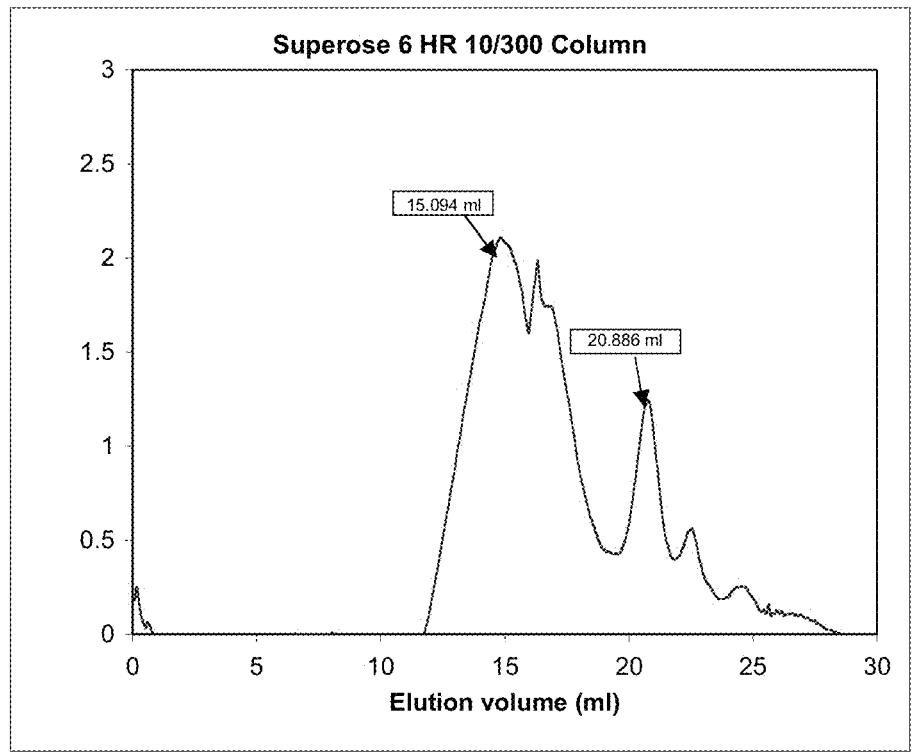
FIG. 18 shows the dynamic relationship of the oligomeric states of hsp20 using FPLC analysis of 29 μM hsp20 in 500 mM NaCl (13.69=16mer; 15.05=10mer; 16.85=hexamer; 17.99=tetramer; 20.18=dimer; 22.72=monomer Dimer=15% of total)

FIG. 18 shows the dynamic relationship of the oligomeric states of hsp20 using FPLC analysis of 29 μM hsp20 in 500 mM NaCl (13.69=16mer; 15.05=1 Omer; 16.85=hexamer; 17.99=tetramer; 20.18=dimer; 22.72=monomer Dimer=15% of total).

Kinetics of Hsp20 fibril prevention activity. Next, it was determined whether Hsp20 simply slowed the rate of aggregation of Aβ or if it altered the aggregation pathway such that non toxic species were formed. This was an important question, as if Hsp20 simply slowed the rate of aggregation, then it would be a much less attractive aggregation inhibitor than if it actually changed the aggregation pathway away from toxic species. As can be seen from FIG. 17, in physiological buffers, Aβ aggregates until approximately 40% of the peptide is incorporated into fibrils by 10 hours, after which time no further increase in Congo red binding is observed. However, in the presence of Hsp20, maximum Congo red binding occurs within 4 hours, after which a loss in Congo red binding is observed. Similar trends were observed in toxicity studies as a function of time with analogously prepared samples. These data suggest that Hsp20 does not simply slow down Aβ aggregation, but alters the Aβ aggregation pathway. A turbidity assay also reveals the same results.

Hsp20 exists in multimeric forms. The existence of the forms is concentration dependent. Only the lowest concentrations with smaller oligomeric forms are active in blocking Aβ fibril formation.

Figure 19:
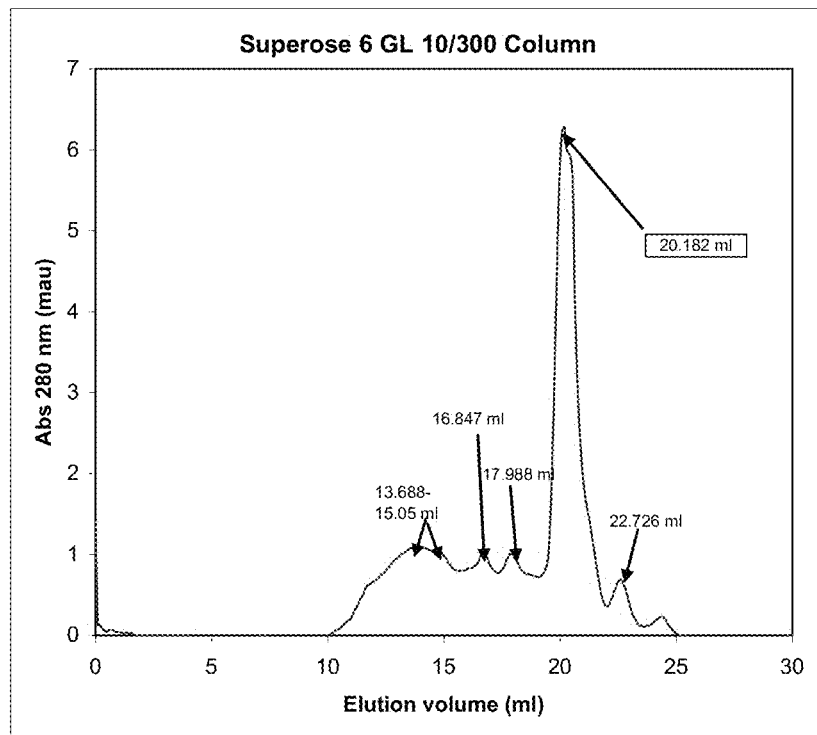
FIG. 19 is a graph that shows the dynamic relationship of the oligomeric states of hsp20.
Figure 22:
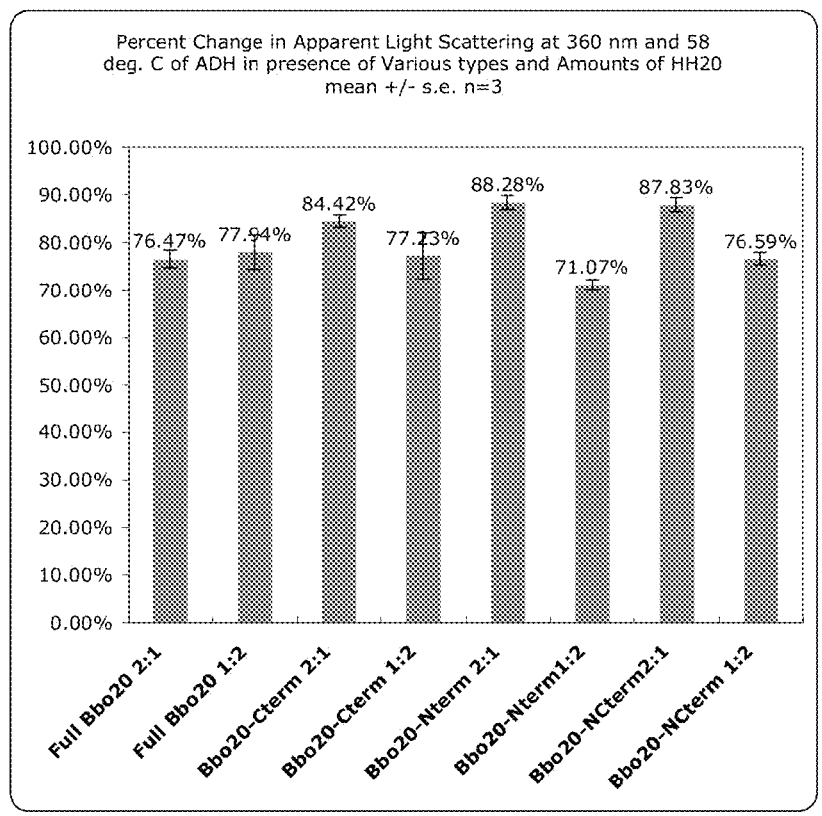
FIG. 22 shows that truncated hsp20 blocks ADH denaturation.
Figure 23:
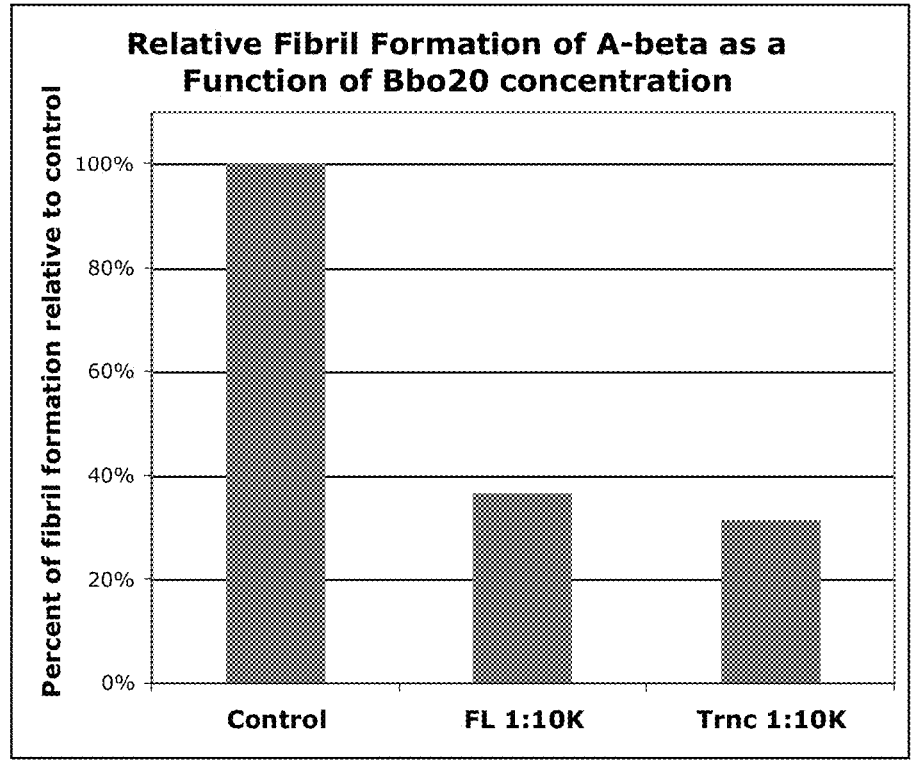
FIG. 23 is a graph that shows that fibril formation of Aβ peptide in the presence of full length and truncated hsp20.

Self-assembly of hsp20 into multimeric complexes. Among α-crystallins that have been well studied, a variety of oligomeric states have been observed and correlated with active and inactive states of the proteins. An analysis of the dynamic relationship of the oligomeric states of hsp20 and their relationship to α-crystallin activity was conducted. One approach that has been successful with the His-tagged protein, and which was largely unsuccessful with the larger MBP fused version is analysis of hsp20 at several concentrations through FPLC. Superose 6 resin (Pharmacia) and size exclusion standards have been used to create a standard curve of elution volume versus standard molecular weight. When purified recombinant his-Hsp20 is applied to the column at intermediate concentrations under high salt conditions, (29 µM) a number of discrete oligomeric states are observed (FIG. 19). Elution volumes correspond to the following multimeric species: 13.69=16mer; 15.05=10mer; 16.85=6mer; 17.99=tetramer; 20.18=dimer; 22.72=monomer. The dimeric form of the protein constitutes approximately 15% of the total hsp20 applied to the column.

At intermediate concentrations (29 µM, FIG. 19) the dimeric species constitutes approximately 42% of the protein eluted from the column. When this same protein solution is diluted further to a final concentration of 0.1 µM, and applied to size exclusion chromatography, the dimer is the predominant species, constituting more than 95% of the eluted protein (not shown), suggestions that an equilibrium exists between species, and that the dimeric form of the protein may be produced selectively by designing experiments at low concentrations of Hsp20. Alternatively, the production of a dimeric species stable at higher concentrations would be advantageous.

In an effort to find the smallest active piece of hsp20 with respect to prevention of ADH denaturation and Aβ fibril formation, hsp20 was truncated at C the and N terminus. All truncated forms prevent ADH denaturation. C-terminal truncation and full length prevent Aβ fibril formation. The other truncated versions (N-terminal and N and C terminal) may also be tested in the fibril assay. The truncated forms were made to stabilize hsp20 in the form which is most active.

Stabilization of specific complexes; alteration of the steady state level of specific species. Based on the X-ray crystallographic analysis of other alpha crystallins the putative hsp20 domains governing assembly of dimers, dodecamers and larger ordered alpha crystalline structures were identified. Using recombinant DNA technology truncations of specific regions of the hsp20 recombinant protein were constructed and tested to show: (1) the equilibrium distribution of oligomer of the truncated protein, (2) activity in an ADH denaturation assay of the truncated protein and, β) amyloid fibril prevention by the altered protein.

FIG. 20 is a sequence alignment of M.j-sHSP and *B. bovis* HSP20: N terminal and C terminal deletions with the C-terminal deletion of HSP20=EMRRVQIDAKA (SEQ ID NO.: 5).

Based on the analysis of an alpha crystalline derived from a thermophilic bacteria by Laksanalamai, et al (2003), the carboxy-terminal 12 amino acids of hsp20 were removed (FIG. 20) in order to reduce or eliminate the assembly of dimers into dodecamers, thus trapping hsp20 in dimer configuration. When the recombinant protein was applied to FPLC (Superose 6 resin), approximately 42% of the preparation migrated as a dimeric species on the column (FIG. 21). These results are in contrast to the full length hsp20 which at equilibrium demonstrates only 1-2% dimer at similar concentrations (Lee, et al., 2005). The carboxy-terminal truncated protein preparation, highly enriched for dimeric species was tested in an ADH assay (FIG. 22) and found to be equivalent in activity to the native protein in that it prevented thermal denaturation of ADH at identical molar ratios (1:2 and 2:1, hsp20:Aβ). When tested in an Aβ assay to prevent fibril formation, a preliminary study showed its activity to also be similar to that of the native preparation (FIG. 21). Further constructs have been made that lack the N terminal 50 amino acids and would be predicted to form dodecamers but lack the ability to form higher order complexes. A third protein lacks both the C-terminal 12 amino acids as well as the N-terminal 50 amino acids. The truncated proteins, which have an intact alpha crystalline domain, are virtually identical in its ability to block ADH denaturation (FIG. 22).

A honeycomb pattern of Aβ-hsp20 complex is detected in EM when ever anti-fibril activity is present (see FIG. 17). After approximately 2 hours of incubating Aβ peptide in the presence of hsp20, an increase in turbidity is seen. This turbidity has proved transient as it then decreases over time. An EM of that 2 hour time point reveals an interesting "honeycomb" pattern which the inventors believe is an Aβ-hsp20 complex. It is not known at this time what the significance of this complex is, however, it may lead to an alternate interaction pathway for Aβ that does not lead to amyloid formation.

FIG. 23 is a graph that shows that fibril formation of Aβ peptide in the presence of full length and truncated hsp20.

The present invention includes a novel small heat shock protein with demonstrable Aβ fibril formation and toxicity prevention activity. Biophysical characterization was performed on the small heat shock protein to determine that it is most likely active as a small oligomer or dimer, which is formed most readily at low concentrations or elevated temperatures. The small heat shock protein disclosed herein prevented both fibril formation and toxicity at very low mole ratios of heat shock protein to Aβ, suggesting that a low abundance Aβ aggregation intermediate interacts with the small heat shock protein. These results show that the small heat shock protein alters the aggregation pathway as opposed to simply altering the rate of aggregation. In addition, stable complexes of Aβ and the small heat shock protein were isolated, which may be used for Aβ aggregation/toxicity prevention.

FIG. 24 shows the amino acid sequences for the full length (SEQ ID NO:13), amino terminal truncated (SEQ ID NO:14), carboxy terminal truncated (SEQ ID NO:15), both the amino and carboxy terminal truncated (SEQ ID NO:16), a his-tagged full length (SEQ ID NO:17), a his-tagged amino terminal truncated (SEQ ID NO:18), a his-tagged carboxy terminal truncated (SEQ ID NO:19), and a his-tagged with both the amino and carboxy terminal truncated (SEQ ID NO:20) proteins that were developed for and are part of the present invention.

Table 1. Coding sequence of *B. bigemina* Hsp 20. The his-tagged is highly related to the *B. bovis* Hsp20. The full-length his-tagged version shows the same protection of ADH aggregation at 58 deg. C. (same method as that used for *B. bovis* HSP20).

Extra amino acids in the His-HSP20 clone:

met-gly-gly-ser-his(6)-gly-met-ala-ser-met-thr-gly-gly-gln-gln-met-gly-arg-asp-leu-TYR-asp(4)-lys-asp-pro-thr-leu-glu-asn-leu-tyr-phe-gln-gly-after cleavage (SEQ ID NO:10), only gly remains.

Entire Coding Sequence (Including Purification Tag and TEV Protease Site):

(SEQ ID NO: 2)
MGGSHHHHHHGMASMTGGQQMGRDLYDDDDKDPTLENLYFQGMSCIM

RCNNSEQEVVIDEQTGLPVKNHDYTEKPSVIYKPSTIVPQNTILEIP

PPKELETPITFNPTVDTFFDADTNKIVVLMELPGFSHNDITVECGLG

ELIISGPRPKDELYEKFGNNLDIHIRERKVGYFYRRFKLPHNALDKS

VAVSYSNGILDIRIECSQFSEMRRIQIDGKA

NA Coding Sequence of Above Protein Sequence:

(SEQ ID NO: 1)
ATGGGGGGTTCTCATCATCATCATCATCATGGTATGGCTAGCATGAC

TGGTGGACAGCAAATGGGTCGGGATCTGTACGACGATGACGATAAGG

ATCCAACCCTTGAAAATCTTTATTTTCAAGGTATGTCGTGCATTATG

AGGTGCAACAACTCCGAACAGGAGGTTGTCATCGATGAGCAGACGGG

ACTCCCAGTGAAGAACCACGACTACACTGAGAAGCCCTCTGTGATTT

ACAAGCCGTCGACCATTGTTCCTCAAAACACCATCCTTGAGATCCCT

CCTCCCAAGGAACTGGAAACCCCTATCACCTTCAACCCCACCGTCGA

CACCTTTTTCGATGCTGACACCAACAAGATCGTTGTTTTGATGGAAC

TGCCTGGATTCAGCCACAACGACATCACTGTGGAGTGCGGTTTGGGA

GAACTCATCATCAGCGGCCCCCGCCCCAAGGACGAGCTTTACGAGAA

GTTCGGTAACAACCTTGACATCCACATCCGTGAGCGCAAGGTTGGTT

ACTTCTACAGGCGCTTCAAGCTCCCGCACAACGCCTTGGACAAGTCT

GTTGCTGTGTCTTACTCCAACGGTATCTTGGACATCAGGATTGAGTG

CTCGCAGTTCTCCGAGATGCGCCGCATCCAGATCGACGGCAAGGCAT

AA

In FIG. 26, the multimeric state of HSP20 (full-length and various deletions) is analyzed by crosslinking. The cross-linked samples are then visualized via electrophoresis on a denaturing 12% polyacrylamide-SDS gel. Briefly, the reaction is carried out in cross-linking buffer (1 mM DTT, 100 nM NaCl, 0.2 mM EDTA, 0.05% v/v NP40, 10% v/v glycerol, 25 mM HEPES, pH 8.0) and the diluted purified protein samples are mixed at a ratio of 1:1 with Cross-linking Buffer. Next, 3 µl of 0.1% glutaraldehyde are added to 27 µl of protein. At 5, 10 and 20 minutes, 10 µl aliquots are withdrawn and combined with 10 µl of tris-glycine buffer (to quench the crosslinker). For loading on SDS-PAGE, an equal volume of 2×SDS loading dye is added and the samples are boiled for 5 minutes and ran on 12% SDS PAGE.

In the figures, high-order structures are seen forming at the top of the gel within 5 minutes. The monomeric protein is depleted over time indicating its role in multimer formation. These figures demonstrate that the full-length forms high-order oligomers. Also, the C-terminal deletion (12 aa), N-terminal deletion (50 aa) and N—C-terminal double deletion (62 aa) seem to still form very high order oligomers despite the fact that ⅓ of the 177-residue protein has been removed. This observation along with the fact that the C-terminal deletion has no affect on its amyloid protection activity or ADH aggregation protection by the N—, C— and N—C-terminal deletions suggest that a much smaller region of the protein is responsible for the activities observed (specifically aggregation and amyloid protection).

FIG. 25 is a gel that shows the effect of the truncations (as listed) on the target protein, and that the monomeric protein is depleted over time indicating its role in multimer formation.

FIG. 26 is a gel that shows the effect of the truncations (as listed) on the target protein, and that the monomeric protein is depleted over time indicating its role in multimer formation.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. Lambert, M. P., Barlow, A. K., Chromy, B. A., Edwards, C., Freed, R., Liosatos, M., Morgan, T. E., Rozovsky, I., Trommer, B., Viola, K. L., Wals, P., Zhang, C., Finch, C. E., Krafft, G. A. & Klein, W. L. (1998) *Proc Natl Acad Sci USA* 95, 6448-53.
2. Iversen, L. L., Mortishire-Smith, R. J., Pollack, S. J. & Shearman, M. S. (1995) *Biochem J* 311 (Pt 1), 1-16.
3. Wang, S. S., Becerra-Arteaga, A. & Good, T. A. (2002) *Biotechnol Bioeng* 80, 50-9.
4. Ward, R. V., Jennings, K. H., Jepras, R., Neville, W., Owen, D. E., Hawkins, J., Christie, G., Davis, J. B., George, A., Karran, E. H. & Howlett, D. R. (2000) *Biochem J* 348 Pt 1, 137-44.
5. Dahlgren, K. N., Manelli, A. M., Stine, W. B., Jr., Baker, L. K., Krafft, G. A. & LaDu, M. J. (2002) *J Biol Chem* 277, 32046-53.
6. Cairo, C. W., Strzelec, A., Murphy, R. M. & Kiessling, L. L. (2002) *Biochemistry* 41, 8620-9.
7. Ghanta, J., Shen, C. L., Kiessling, L. L. & Murphy, R. M. (1996) *J Biol Chem* 271, 29525-8.
8. Pallitto, M. M., Ghanta, J., Heinzelman, P., Kiessling, L. L. & Murphy, R. M. (1999) *Biochemistry* 38, 3570-8.
9. Lansbury, P. T., Jr. (1997) *Curr Opin Chem Biol* 1, 260-7.

10. Tjernberg, L. O., Naslund, J., Lindqvist, F., Johansson, J., Karlstrom, A. R., Thyberg, J., Terenius, L. & Nordstedt, C. (1996) *J Biol Chem* 271, 8545-8.
11. Kudva, Y. C., Hidding a, H. J., Butler, P. C., Mueske, C. S. & Eberhardt, N. L. (1997) *FEBS Lett* 416, 117-21.
12. Stege, G. J., Renkawek, K., Overkamp, P. S., Verschuure, P., van Rijk, A. F., Reijnen-Aalbers, A., Boelens, W. C., Bosman, G. J. & de Jong, W. W. (1999) *Biochem Biophys Res Commun* 262, 152-6.
13. Brown, W. C., Ruef, B. J., Norimine, J., Kegerreis, K. A., Suarez, C. E., Conley, P. G., Stich, R. W., Carson, K. H. & Rice-Ficht, A. C. (2001) *Mol Biochem Parasitol* 118, 97-109.
14. Klunk, W. E., Jacob, R. F. & Mason, R. P. (1999) *Anal Biochem* 266, 66-76.
15. Horwitz, J. (1992) *Proc Natl Acad Sci USA* 89, 10449-53.
16. van den, I. P., Norman, D. G. & Quinlan, R. A. (1999) *Curr Biol* 9, R103-5.
17. Bruey, J. M., Ducasse, C., Bonniaud, P., Ravagnan, L., Susin, S. A., Diaz-Latoud, C., Gurbuxani, S., Arrigo, A. P., Kroemer, G., Solary, E. & Gamido, C. (2000) *Nat Cell Biol* 2, 645-52.
18. Jakob, U., Gaestel, M., Engel, K. & Buchner, J. (1993) *J Biol Chem* 268, 1517-20.
19. MacRae, T. H. (2000) *Cell Mol Life Sci* 57, 899-913.
20. van Montfort, R. L., Basha, E., Friedrich, K. L., Slingsby, C. & Vierling, E. (2001) *Nat Struct Biol* 8, 1025-30.
21. Horwitz, J. (2000) *Semin Cell Dev Biol* 11, 53-60.
22. Hughes, S. R., Khorkova, O., Goyal, S., Knaeblein, J., Heroux, J., Riedel, N. G. & Sahasrabudhe, S. (1998) *Proc Natl Acad Sci USA* 95, 3275-80.
23. Hatters, D. M., Lindner, R. A., Carver, J. A. & Howlett, G. J. (2001) *J Biol Chem* 276, 33755-61.
24. Abgar, S., Vanhoudt, J., Aerts, T. & Clauwaert, J. (2001) *Biophys J* 80, 1986-95.
25. Lomakin, A., Teplow, D. B., Kirschner, D. A. & Benedek, G. B. (1997) *Proc Natl Acad Sci USA* 94, 7942-7.
26. Pallitto, M. M. & Murphy, R. M. (2001) *Biophys J* 81, 1805-22.
27. Yong, W., Lomakin, A., Kirkitadze, M. D., Teplow, D. B., Chen, S. H. & Benedek, G. B. (2002) *Proc Natl Acad Sci USA* 99, 150-4.
28. McHaourab, H. S., Dodson, E. K. & Koteiche, H. A. (2002) *J Biol Chem* 277, 40557-66.
29. Liang, J. J. (2000) *FEBS Lett* 484, 98-101.
30. Soto, C., Sigurdsson, E. M., Morelli, L., Kumar, R. A., Castano, E. M. & Frangione, B. (1998) *Nat Med* 4, 822-6.
31. Hetenyi, C., Szabo, Z., Klement, E., Datki, Z., Kortvelyesi, T., Zarandi, M. & Penke, B. (2002) *Biochem Biophys Res Commun* 292, 931-6.

What is claimed is:

1. An isolated and purified polypeptide comprising a portion of an α-crystallin polypeptide comprising one or more β-pleated sheets that at least one of inhibits neurotoxicity, inhibits amyloidogenesis, or stabilizes hsp20, and is selected from SEQ ID NOs: 18 to 20.

2. The polypeptide of claim 1, wherein the polypeptide is non-human.

3. The polypeptide of claim 1, wherein the polypeptide is from a bovine erythrocyte parasite.

4. The polypeptide of claim 1, wherein the polypeptide is from a *Babesia* sp. bovine erythrocyte parasite.

5. The polypeptide of claim 1, wherein the polypeptide is from a *Babesia bovis*.

6. The polypeptide of claim 1, wherein the polypeptide comprises Hsp20.

7. An isolated and purified heat shock protein comprising one or more β-pleated sheets that modulates neurotoxicity over about a one-thousand-fold concentration range by stabilizing an amyloidogenic protein, wherein the protein is selected from SEQ ID NOs: 18 to 20.

8. The protein of claim 7, wherein the concentration range is between about 1 nM to about 5 μM.

9. The protein of claim 7, wherein the molar ratios of heat shock protein to amyloidogenic protein is between about 0.0005 to about 0.001.

10. An isolated and purified portion of a polypeptide of the α-crystallin family of proteins and comprising one or more β-pleated sheets isolated from *Babesia* sp. selected from SEP ID NOS: 18 to 20.

11. An isolated or purified heat shock protein truncated at the amino, carboxy or amino and carboxy terminus Hsp20 protein that inhibits Aβ1-40 fibril formation selected from SEQ ID NOs: 18 to 20.

12. A pharmaceutical composition for treating amyloidogenesis comprising: an effective amount of a purified polypeptide with α-crystallin activity and one or more β-pleated sheets that at least one of inhibits neurotoxicity, inhibits amyloidogenesis or stabilizes hsp20 in pharmaceutically acceptable carrier selected from SEQ ID NOs: 18 to 20.

13. An isolated and purified polypeptide comprising an α-crystallin, small, heat shock protein Hsp20 having one or more β-pleated sheets that inhibits neurotoxicity and amyloidogenesis selected from SEQ ID NOs: 18 to 20.

14. The polypeptide of claim 13, wherein the polypeptide is from a *Babesia bovis*.

15. The polypeptide of claim 13, wherein the polypeptide interferes with intermediate forms of amyloid.

* * * * *